United States Patent
Shimizu

(10) Patent No.: US 10,457,622 B2
(45) Date of Patent: Oct. 29, 2019

(54) METHOD FOR PRODUCING ACETIC ACID

(71) Applicant: DAICEL CORPORATION, Osaka-shi, Osaka (JP)

(72) Inventor: Masahiko Shimizu, Himeji (JP)

(73) Assignee: DAICEL CORPORATION, Osaka-Shi (JP)

( * ) Notice: Subject to any disclaimer, the term of this patent is extended or adjusted under 35 U.S.C. 154(b) by 0 days.

(21) Appl. No.: 15/542,833

(22) PCT Filed: May 25, 2017

(86) PCT No.: PCT/JP2017/019576
§ 371 (c)(1),
(2) Date: Jul. 11, 2017

(87) PCT Pub. No.: WO2018/163448
PCT Pub. Date: Sep. 13, 2018

(65) Prior Publication Data
US 2018/0258022 A1 Sep. 13, 2018

(30) Foreign Application Priority Data
Mar. 8, 2017 (JP) ................ 2017-044341

(51) Int. Cl.
C07C 51/12 (2006.01)
C07C 51/44 (2006.01)
B01D 3/00 (2006.01)
B01D 3/14 (2006.01)
C07C 51/47 (2006.01)

(52) U.S. Cl.
CPC .............. *C07C 51/12* (2013.01); *B01D 3/009* (2013.01); *B01D 3/143* (2013.01); *C07C 51/44* (2013.01); *C07C 51/445* (2013.01); *C07C 51/47* (2013.01)

(58) Field of Classification Search
CPC ..................................... C07C 51/12
See application file for complete search history.

(56) References Cited

U.S. PATENT DOCUMENTS

| 5,696,284 A | 12/1997 | Baker et al. |
| 2013/0264186 A1 | 10/2013 | Shimizu et al. |
| 2015/0368176 A1 | 12/2015 | Miura et al. |
| 2016/0130207 A1* | 5/2016 | You ..................... B01J 31/181 562/519 |
| 2016/0289154 A1 | 10/2016 | Scates et al. |

FOREIGN PATENT DOCUMENTS

| EP | 0 749 948 A1 | 12/1996 |
| EP | 2 949 640 A1 | 12/2015 |
| EP | 3002057 A1 | 4/2016 |
| JP | 9-2993 A | 1/1997 |
| JP | 2014-508820 A | 4/2014 |
| WO | WO 2012/086386 A1 | 6/2012 |
| WO | WO 2012/092360 A1 | 7/2012 |
| WO | WO 2014/115826 A1 | 7/2014 |
| WO | WO 2016/076972 A1 | 5/2016 |
| WO | WO 2016/122728 A1 | 8/2016 |
| WO | WO 2017/083668 A1 | 5/2017 |

OTHER PUBLICATIONS

International Search Report dated Aug. 8, 2017, in PCT International Application No. PCT/JP2017/019576.
Written Opinion dated Aug. 8, 2017, in PCT International Application No. PCT/JP2017/019576.
English tranlsation of the Written Opinion dated Oct. 9, 2017, in PCT International Application No. PCT/JP2017/019576.
Extended European Search Report for Application No. 17737195.2, dated Mar. 1, 2018.
Japanese Notification of Reasons for Rejection for Application No. 2017-536032, dated Jul. 3, 2018, with English language translation.

* cited by examiner

*Primary Examiner* — Ana Z Muresan
(74) *Attorney, Agent, or Firm* — Birch, Stewart, Kolasch & Birch, LLP

(57) ABSTRACT

Provided is a method for producing acetic acid that is capable of greatly improving the life of a silver-substituted ion exchange resin (IER) for removing organic iodine compounds in acetic acid.
With the method for producing acetic acid according to the present invention, in a carbonylation process of a methanol method, a nickel base alloy or zirconium is used as a material of a distillation column in a dehydration step, and as metal ion concentrations in a charging mixture of the distillation column in the dehydration step, an iron ion concentration is less than 10,000 ppb by mass, a chromium ion concentration is less than 5,000 ppb by mass, a nickel ion concentration is less than 3,000 ppb by mass, and a molybdenum ion concentration is less than 2,000 ppb by mass.

20 Claims, 5 Drawing Sheets

[Figure 1]
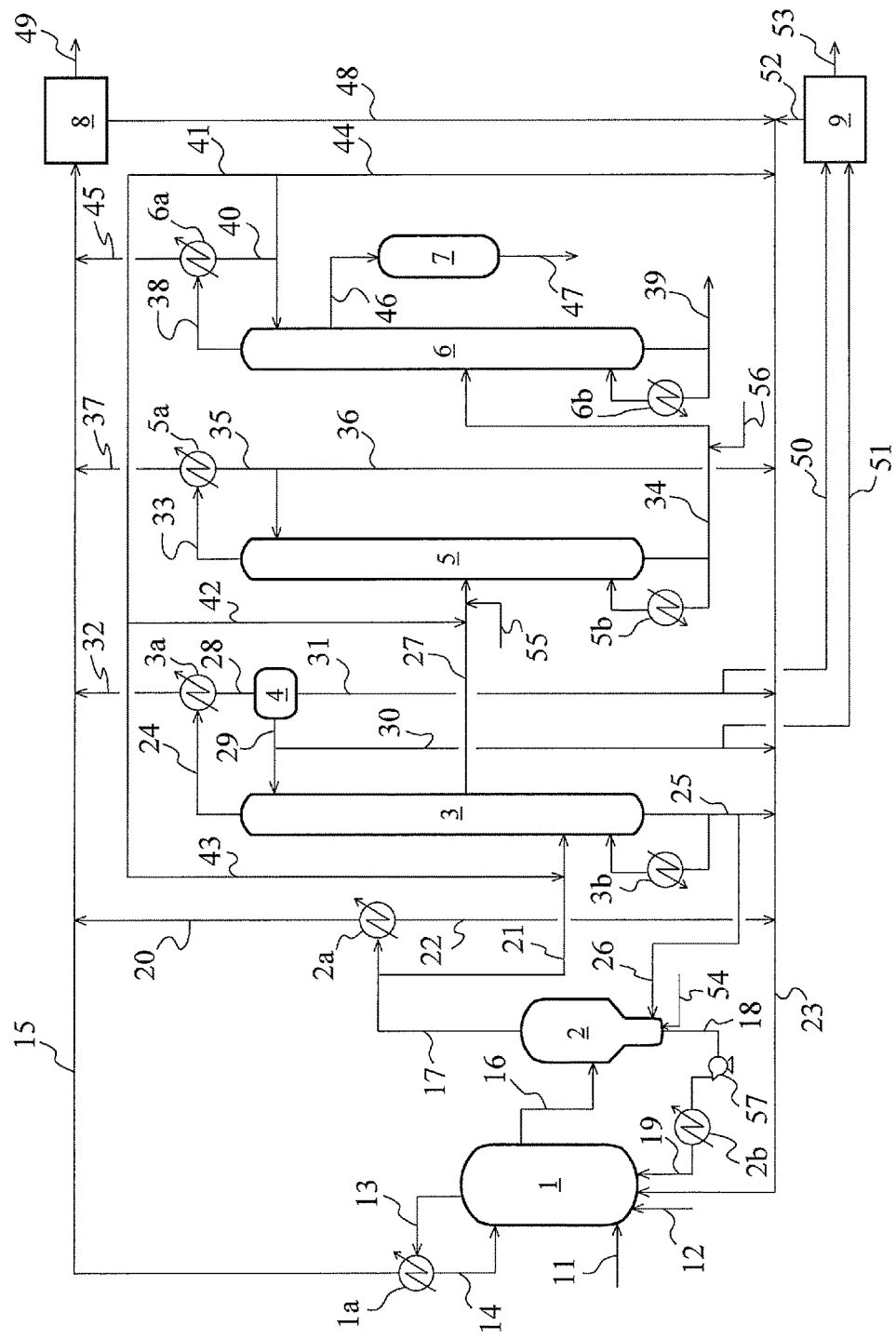

[Figure 2]
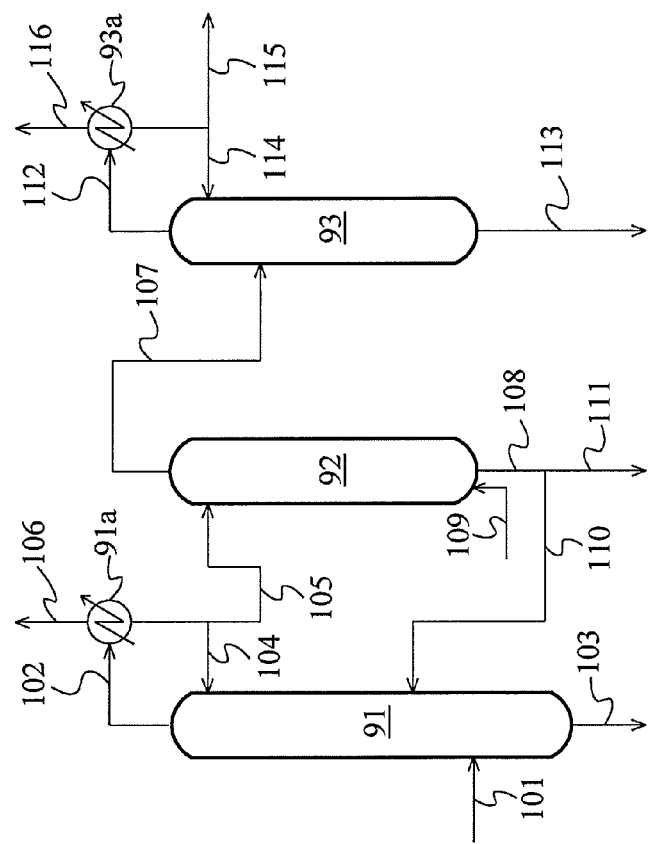

[Figure 3]
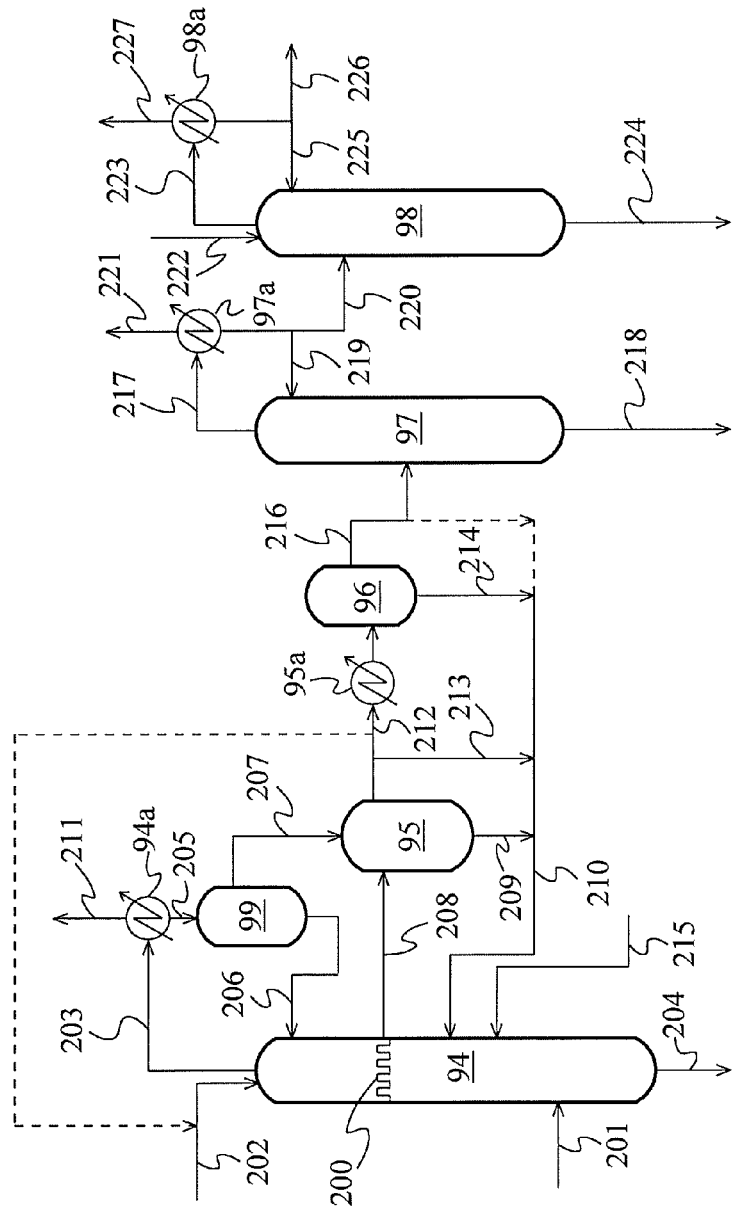

[Figure 4]
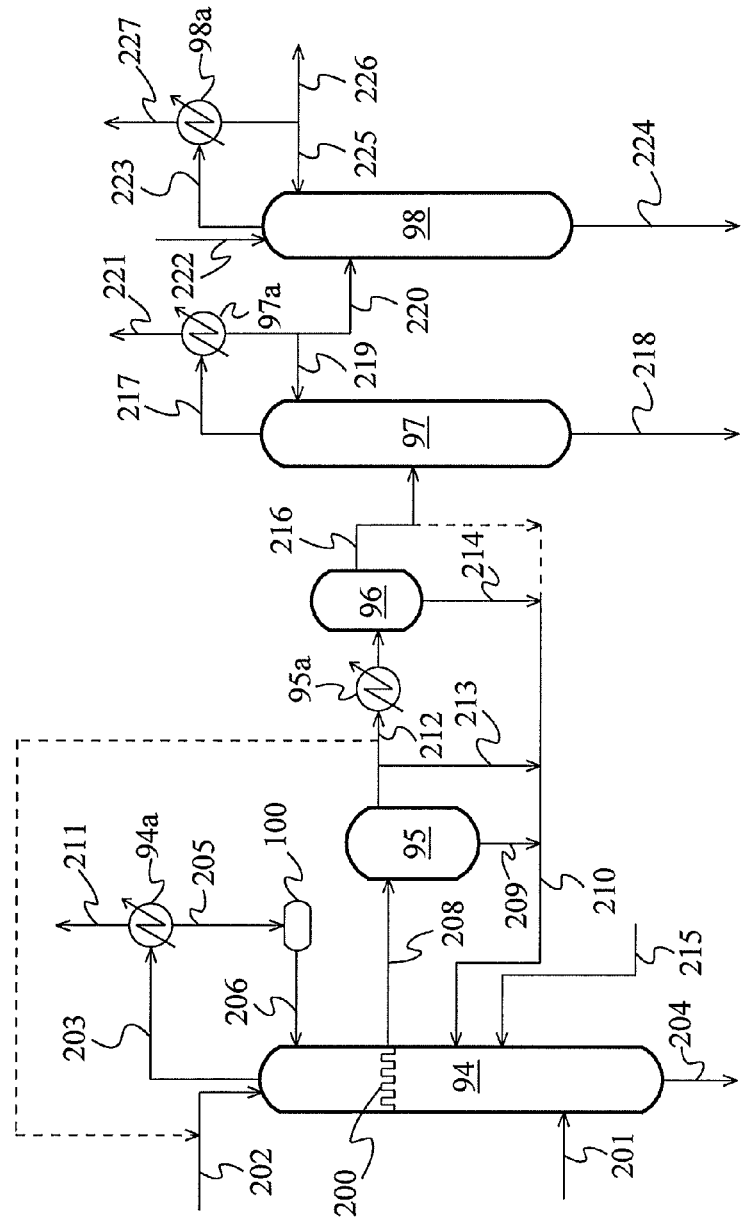

[Figure 5]
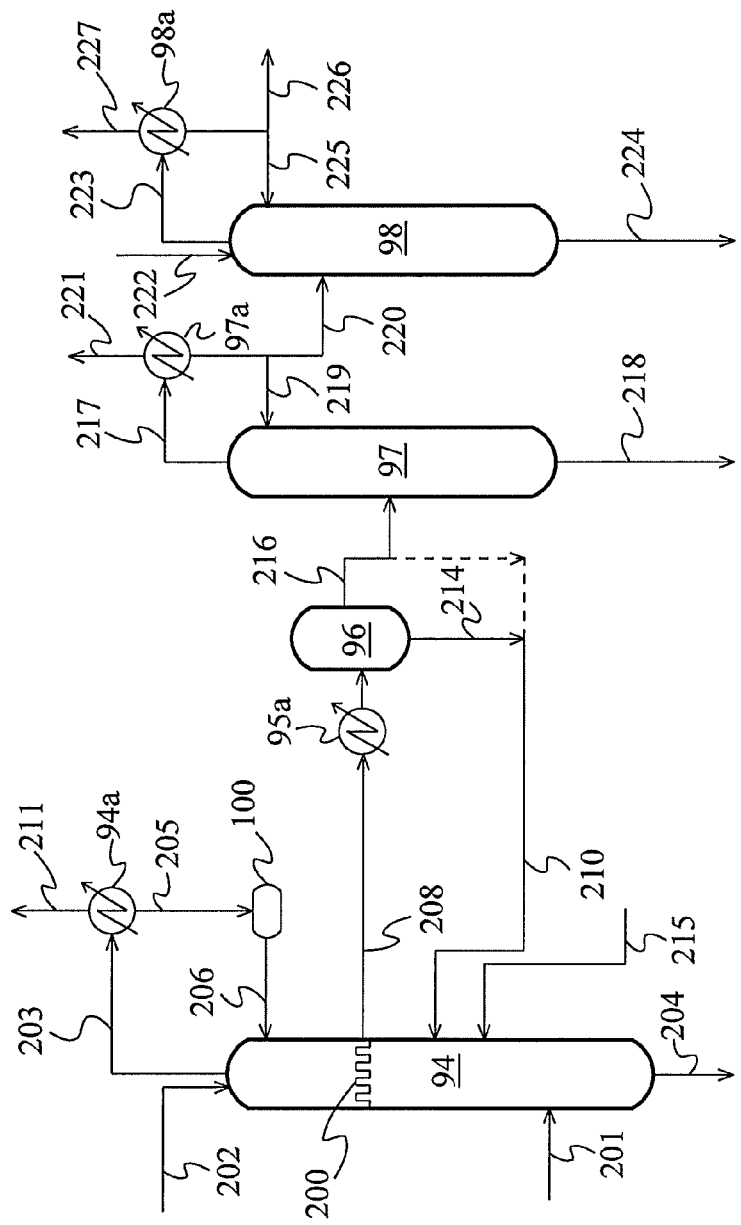

METHOD FOR PRODUCING ACETIC ACID

TECHNICAL FIELD

The present invention relates to a method for producing acetic acid. The present application claims the priority of Japanese Patent Application No. 2017-044341 filed in Japan on Mar. 8, 2017, the contents of which are incorporated herein by reference in their entirety.

BACKGROUND ART

A carbonylation process of a methanol method (an acetic acid process of a methanol method) is known as an industrial method for producing acetic acid. In this process, for example, methanol and carbon monoxide are reacted in the presence of a catalyst in a reaction vessel to produce acetic acid. The reaction mixture is evaporated in an evaporator, and the vapor phase is purified in a lower boiling point component removal column and subsequently in a dehydration column so that product acetic acid is prepared. Alternatively, product acetic acid is prepared via a higher boiling point component removal column subsequent to the dehydration column, and further, a product column.

In such a process for producing acetic acid, organic iodine compounds, such as hexyl iodide, are produced as by-products in the reaction system, and are included as a very small amount of impurities in the product acetic acid. When acetic acid containing organic iodine compounds is used as a raw material for producing vinyl acetate, the palladium catalyst is degraded, and hence there is a need to reduce the organic iodine compound concentration in the acetic acid to an order of a few ppb. Therefore, conventionally, the organic iodine compound concentration in the acetic acid has been reduced to as low as possible by using a cation exchange resin substituted with silver ions. However, in an adsorptive removal method of organic iodine compounds that uses such a silver-substituted ion exchange resin (hereinafter, sometimes referred to as an "IER"), there is a problem that corroded metals (also referred to as "corrosion metals") derived from corrosion in an apparatus, such as iron, nickel, chromium, and molybdenum, and the like present in the process stream undergo ion exchange with the silver in the ion exchange resin, whereby useful silver dissolves into the acetic acid and flows out of the system, causing the organic iodine compound removal life of the ion exchange resin to decrease. Further, as a consequence of that, there is also the problem that the concentration of corrosion metals etc. and the silver concentration in the product acetic acid increase, causing the quality of the product acetic acid to deteriorate.

Patent Literature 1 discloses, a process in which, in order to suppress deterioration in the life of an ion exchange resin due to corroded metals, acetic acid is purified using an ion exchange resin composition including a metal-activated ion exchange resin containing a specific amount of metal-functionalized sites and a non-metal-functionalized ion exchange resin containing non-metal-functionalized sites. Further, Patent Literature 2 discloses a method in which, in order to suppress corrosion of a dehydration column, an alkali component for neutralizing hydrogen iodide, which is a factor in apparatus corrosion, is added and mixed into the dehydration column or the dehydration column feeding solution.

However, none of the above-described methods are capable of sufficiently suppressing deterioration in the life of the ion exchange resin due to corroded metals.

CITATION LIST

Patent Literature

Patent Literature 1: National Publication of International Patent Application No. 2014-508820
Patent Literature 2: International Patent Application No. 2012/086386

SUMMARY OF INVENTION

Technical Problem

Accordingly, an object of the present invention is to provide a method for producing acetic acid capable of greatly improving the life of a silver-substituted ion exchange resin (IER) for removing organic iodine compounds in acetic acid.

Solution to Problem

In order to attain the object, the present inventors have conducted diligent studies focusing on the material of the dehydration column and impurities in the charging mixture of the dehydration column to discover that, by employing a specific material for the material of the dehydration column, and controlling the concentrations of specific metal ions in the dehydration column charging mixture, the metal ion concentrations in the acetic acid obtained from the dehydration column can be maintained at a low level, the metal ion concentrations in the acetic acid fed into the IER in a subsequent adsorptive removal step can be controlled to a low level, thus the life of the IER can be greatly improved, and therefore the deterioration of the quality of the product acetic can be prevented, to thereby complete the present invention.

Specifically, the present invention provides a method for producing acetic acid, including:
a carbonylation reaction step of reacting methanol with carbon monoxide in a reaction vessel in the presence of a catalyst system containing a metal catalyst and methyl iodide as well as acetic acid, methyl acetate, and water to produce acetic acid;
an evaporation step of separating a reaction mixture obtained in the carbonylation reaction step into a vapor stream and a residual liquid stream in an evaporator;
a lower boiling point component removal step of separating the vapor stream by distillation into an overhead stream rich in at least one lower boiling point component selected from methyl iodide and acetaldehyde and a first acetic acid stream rich in acetic acid;
a dehydration step of separating the first acetic acid stream by distillation into an overhead stream rich in water and a second acetic acid stream more enriched with acetic acid than the first acetic acid stream; and
an adsorptive removal step of treating the second acetic acid stream, or an acetic acid stream that has been more enriched with acetic acid by further purification of the second acetic acid stream, with an ion exchange resin,
wherein a nickel base alloy or zirconium is used as a material of a distillation column in the dehydration step, and as metal ion concentrations in a charging mixture of the distillation column in the dehydration step, an iron ion concentration is less than 10,000 ppb by mass, a chromium ion concentration is less than 5,000 ppb by mass, a nickel ion concentration is less than 3,000 ppb by mass, and a molybdenum ion concentration is less than 2,000 ppb by mass.

The catalyst system may further include an ionic iodide.

It is preferred that a zinc ion concentration in the charging mixture of the distillation column in the dehydration step be less than 1,000 ppb by mass.

It is preferred that operating conditions of the distillation column in the dehydration step be a column top temperature of less than 165° C. and a column bottom temperature of less than 175° C.

It is preferred that an iron ion concentration in the second acetic acid stream obtained in the dehydration step be less than 21,000 ppb by mass.

It is preferred that as the metal ion concentrations in the second acetic acid stream obtained in the dehydration step, the iron ion concentration be less than 21,000 ppb by mass, a chromium ion concentration be less than 7,100 ppb by mass, a nickel ion concentration be less than 4,000 ppb by mass, a molybdenum ion concentration be less than 3,000 ppb by mass, and a zinc ion concentration be less than 1,000 ppb by mass.

It is preferred that a plate spacing between a charging mixture feeding plate and a column top vapor withdrawal plate of the distillation column in the dehydration step be not less than one plate in terms of actual plates.

It is preferred that the material of a charging pipe to the distillation column in the dehydration step be a nickel base alloy or zirconium.

The present invention also provides a method for producing acetic acid, comprising, in a distillation column having a nickel base alloy or zirconium as a material and having a plate spacing between a charging mixture feeding plate and a column top vapor withdrawal plate of not less than one plate in terms of actual plates, feeding crude acetic acid having an iron ion concentration of less than 10,000 ppb by mass, a chromium ion concentration of less than 5,000 ppb by mass, a nickel ion concentration of less than 3,000 ppb by mass, a molybdenum ion concentration of less than 2,000 ppb by mass, a zinc ion concentration of less than 1,000 ppb by mass, a hexyl iodide concentration of less than 510 ppb by mass, and an acetic acid concentration of not less than 80% by mass into the charging mixture feeding plate via a charging pipe having a nickel base alloy or zirconium as a material, and conducting distillation at a column top temperature of less than 165° C. and a column bottom temperature of less than 175° C. to obtain an overhead stream rich in water, and purified acetic acid having an iron ion concentration of less than 21,000 ppb by mass, a chromium ion concentration of less than 7,100 ppb by mass, a nickel ion concentration of less than 4,000 ppb by mass, a molybdenum ion concentration of less than 3,000 ppb by mass, and a zinc ion concentration of less than 1,000 ppb by mass.

Advantageous Effects of Invention

According to the present invention, because the distillation column (hereinafter, sometimes referred to as a "dehydration column") in a dehydration step is formed of a specific material, and the concentrations of specific metal ions in the charging mixture to the dehydration column are specified as being not more than certain values, the metal ion concentrations in the purified acetic acid obtained at the dehydration column can be reduced, and because of that, the metal ion concentrations in the acetic acid fed to the subsequent adsorptive removal step can also be reduced. As a result, the life of the silver-substituted ion exchange resin (IER) used in the adsorptive removal step can be greatly improved, and the metal ion concentrations in the product acetic acid can also be reduced. The resultant acetic acid having low metal ion concentrations can be utilized as low-metal acetic acid that can be used in electronic material applications.

BRIEF DESCRIPTION OF DRAWINGS

FIG. 1 is an acetic acid production flow diagram showing one embodiment of the present invention.

FIG. 2 is a schematic flow diagram showing one example of an acetaldehyde separation and removal system.

FIG. 3 is a schematic flow diagram showing another example of the acetaldehyde separation and removal system.

FIG. 4 is a schematic flow diagram showing a further alternative example of the acetaldehyde separation and removal system.

FIG. 5 is a schematic flow diagram showing a further alternative example of the acetaldehyde separation and removal system.

DESCRIPTION OF EMBODIMENTS

The method for producing acetic acid according to the present invention includes: a carbonylation reaction step of reacting methanol with carbon monoxide in a reaction vessel in the presence of a catalyst system containing a metal catalyst and methyl iodide as well as acetic acid, methyl acetate, and water to produce acetic acid; an evaporation step of separating a reaction mixture obtained in the carbonylation reaction step into a vapor stream and a residual liquid stream in an evaporator; a lower boiling point component removal step of separating the vapor stream by distillation into an overhead stream rich in at least one lower boiling point component selected from methyl iodide and acetaldehyde and a first acetic acid stream rich in acetic acid; a dehydration step of separating the first acetic acid stream by distillation into an overhead stream rich in water and a second acetic acid stream more enriched with acetic acid than the first acetic acid stream; and an adsorptive removal step of treating the second acetic acid stream, or an acetic acid stream that has been more enriched with acetic acid by further purification of the second acetic acid stream, with an ion exchange resin. In this method for producing acetic acid, a nickel base alloy or zirconium is used as the material of the distillation column (dehydration column) in the dehydration step, and the metal ion concentrations in the charging mixture of the dehydration column are controlled such that the iron ion concentration is less than 10,000 ppb by mass, the chromium ion concentration is less than 5,000 ppb by mass, the nickel ion concentration is less than 3,000 ppb by mass, and the molybdenum ion concentration is less than 2,000 ppb by mass. It is preferred that the zinc ion concentration in the charging mixture of the dehydration column be less than 1,000 ppb by mass. The expression "charging mixture of the dehydration column" refers to the whole stream fed to the dehydration column, including at least a part of the first acetic acid stream, and to which a stream other than the first acetic acid stream (e.g., a recycle stream from a downstream step) may be added. The catalyst system may further include an ionic iodide.

The nickel base alloy is an alloy based on nickel. Examples thereof may include Hastelloy (Hastelloy B2, Hastelloy C, etc.), Monel, Inconel, Incoloy, and the like.

The iron ions, chromium ions, nickel ions, and molybdenum ions mentioned above are metal ions produced by corrosion of the apparatus (i.e., are corroded metal ions). On the other hand, the zinc ions are derived from zinc ions contained as impurities in the methanol used as a reaction raw material.

By employing a nickel base alloy or zirconium, which has higher corrosion resistance than a nickel base alloy, for the material of the dehydration column, corrosion of the apparatus by the hydrogen iodide or the acetic acid produced by the reaction system and included in the charging mixture of the dehydration column and the resultant elution of corroded metal ions can be greatly suppressed. Therefore, controlling the amount of specific metal ions flowing into the dehydration column and suppressing the elution of the specific metal ions in the dehydration column enable the concentration of the specific metal ions in the purified acetic acid obtained at the dehydration column to be greatly reduced. As a result, the amount of the specific metal ions flowing to the subsequent adsorptive removal step can be reduced, and the life of the silver-substituted ion exchange resin (IER) used in that step can be greatly improved. Further, as a consequence of that, the metal ion concentrations in the purified acetic acid obtained in the adsorptive removal step can be reduced, and high-quality product acetic acid can be produced for a long time without exchanging the IER for a long period of time. When stainless steel, for example, is employed as the material of the dehydration column, the inner portions of the dehydration column are corroded by hydrogen iodide and acetic acid, a large amount of corroded metals, such as iron, chromium, nickel, and molybdenum, are mixed into the purified acetic acid, and the life of the IER used in subsequent steps is reduced. Further, when the concentrations of the specific metal ions in the charging mixture of the dehydration column are higher than the above-described ranges as well, the metal concentrations in the above-mentioned purified acetic acid increase, and as a result the life of the IER used in subsequent steps is shortened.

It is preferred that the iron ion concentration in the charging mixture of the dehydration column be less than 9,000 ppb by mass, more preferably less than 5,000 ppb by mass, further preferably less than 3,000 ppb by mass, particularly preferably less than 1,500 ppb by mass, and especially less than 800 ppb by mass (e.g., less than 400 ppb by mass). It is preferred that the chromium ion concentration in the charging mixture be less than 4,000 ppb by mass, more preferably less than 2,500 ppb by mass, further preferably less than 1,500 ppb by mass, particularly preferably less than 750 ppb by mass, and especially less than 400 ppb by mass (e.g., less than 200 ppb by mass). It is preferred that the nickel ion concentration in the charging mixture be less than 2,500 ppb by mass, more preferably less than 2,000 ppb by mass, further preferably less than 1,000 ppb by mass, particularly preferably less than 500 ppb by mass, and especially less than 250 ppb by mass (e.g., less than 150 ppb by mass). It is preferred that the molybdenum ion concentration in the charging mixture be less than 1,700 ppb by mass, more preferably less than 1,200 ppb by mass, further preferably less than 700 ppb by mass, particularly preferably less than 350 ppb by mass, and especially less than 170 ppb by mass. Further, it is preferred that the zinc ion concentration in the charging mixture be less than 800 ppb by mass, more preferably less than 650 ppb by mass, further preferably less than 500 ppb by mass, particularly preferably less than 410 ppb by mass, and especially less than 200 ppb by mass.

Examples of the method for controlling the concentrations of the specific metal ions in the charging mixture of the dehydration column to be within the above-described specific ranges may include: (i) employing a metal having high corrosion resistance, such as a nickel base alloy or zirconium, as the material of the charging pipe to the dehydration column; (ii) providing an ion exchange resin (in particular, a cation exchange resin) column (or vessel) for adsorptive removal of the specific metal ions at a suitable position between an outlet of the reaction vessel and an inlet of the dehydration column; and (iii) using methanol having a very low metal ion content (e.g., zinc ion content) as the methanol to be fed to the reaction vessel. Because water, hydrogen iodide, and acetic acid are present in the charging mixture of the dehydration column, the charging pipe to the dehydration column tends to corrode. However, by employing a metal having high corrosion resistance, such as a nickel base alloy or zirconium, for the material of the charging pipe, corrosion of the inner portions of the charging pipe and the resultant elution of corroded metal ions into the dehydration column charging mixture can be suppressed, which enables the metal ion concentrations in the dehydration column charging mixture to be reduced. Further, by providing an ion exchange resin treatment column (or vessel) for adsorptive removal of the specific metal ions at a suitable position between an outlet of the reaction vessel and an inlet of the dehydration column, the metal ions that have flowed along a path from the reaction system to immediately before the ion exchange resin treatment column (or vessel) or the metal ions that have been generated in the path can be removed, and the concentrations of the specific metal ions in the dehydration column charging mixture can be reduced to the above-described specific ranges. In addition, the inner surfaces of the tanker and the tank to be used for transporting and storing the methanol are coated with an inorganic zinc based coating material in order to prevent iron rust from occurring when drying. However, the zinc in the coating material is known to be eluted into the methanol during long-term transportation and storage. Therefore, methanol that is distributed on the market often contains zinc. This zinc is also a factor in reducing the life of the silver-substituted ion exchange resin (IER) used in the adsorptive removal step. Therefore, as the methanol to be used as a raw material in the reaction system, it is preferred that methanol containing as little zinc ions as possible be used. For methanol having a high zinc ion content, it is preferred that such methanol be fed to the reaction system after reducing the zinc ion concentration by, for example, treating with a cation exchange resin. The zinc ion concentration in the raw material methanol used in the reaction system is, for example, less than 10 ppm by mass, preferably less than 1 ppm by mass, further preferably less than 500 ppb by mass, and particularly preferably less than 100 ppm by mass. As described above, the zinc ions derived from the raw material methanol can be removed by providing an ion exchange resin (in particular, a cation exchange resin) column (or vessel) at a suitable position between an outlet of the reaction vessel and an inlet of the dehydration column.

It is preferred that operating conditions of the distillation column (dehydration column) in the dehydration step be a column top temperature of less than 165° C. and a column bottom temperature of less than 175° C. Controlling the column top temperature and the column bottom temperature in the above-described ranges enables the above-described corrosion of the inner portions of the distillation column by the hydrogen iodide and acetic acid to be suppressed, and the corroded metal ion concentrations in the purified acetic acid obtained in the dehydration step to be suppressed. It is more preferred that the column top temperature of the dehydration column be less than 163° C., further preferably less than 161° C., and particularly preferably less than 160° C. The lower limit of the column top temperature of the dehydration column is, for example, 110° C. It is more preferred that the column bottom temperature of the dehydration column be less than 173° C., further preferably less than 171° C., and particularly preferably less than 165° C. The lower limit of the column bottom temperature is, for example, 120° C.

When the number of plates between the dehydration column feeding plate and the column top vapor withdrawal plate is small, entrainment causes corroded metals in the charging mixture to flow out from the column top, and be recycled in the reaction system, for example. Therefore, although the metal concentrations in the purified acetic acid decrease, the originally intended concentration and separation efficiency of the water is reduced. As a result, it is preferred that the plate spacing (number of plates) between the charging mixture feeding plate (feeding plate) and the column top vapor withdrawal plate of the dehydration column be, in terms of actual plates, not less than 1 plate, more preferably not less than 3 plates, further preferably not less than 5 plates, and particularly preferably not less than 8 plates (among other things, not less than 10 plates).

Thus, in the present invention, because a specific material is employed for the material of the dehydration column, and the concentrations of specific metal ions in the dehydration column charging mixture are controlled to be not more than certain values, the metal ion concentrations in the second acetic acid steam, which is obtained as a side stream or a bottom stream of the dehydration column, can be reduced. The iron ion concentration in the second acetic acid stream is, for example, less than 21,000 ppb by mass, preferably less than 16,000 ppb by mass, more preferably less than 6,000 ppb by mass, further preferably less than 2,000 ppb by mass, and particularly preferably less than 200 ppb by mass. The chromium ion concentration in the second acetic acid stream is, for example, less than 7,100 ppb by mass, preferably less than 5,000 ppb by mass, more preferably less than 3,000 ppb by mass, further preferably less than 1,000 ppb by mass, and particularly preferably less than 100 ppb by mass. The nickel ion concentration in the second acetic acid stream is, for example, less than 4,000 ppb by mass, preferably less than 3,000 ppb by mass, more preferably less than 1,800 ppb by mass, further preferably less than 700 ppb by mass, and particularly preferably less than 70 ppb by mass. The molybdenum ion concentration in the second acetic acid stream is, for example, less than 3,000 ppb by mass, preferably less than 2,500 ppb by mass, more preferably less than 1,500 ppb by mass, further preferably less than 500 ppb by mass, and particularly preferably less than 50 ppb by mass. The zinc ion concentration in the second acetic acid stream are, for example, less than 1,000 ppb by mass, preferably less than 850 ppb by mass, more preferably less than 710 ppb by mass, further preferably less than 410 ppb by mass, and particularly preferably less than 150 ppb by mass.

In one preferred aspect of the present invention, in a distillation column having a nickel base alloy or zirconium as a material and having a plate spacing between a charging mixture feeding plate and a column top vapor withdrawal plate of not less than one plate in terms of actual plates (the theoretical number of plates being, for example, not less than 0.5), an overhead stream rich in water and purified acetic acid having an iron ion concentration of less than 21,000 ppb by mass, a chromium ion concentration of less than 7,100 ppb by mass, a nickel ion concentration of less than 4,000 ppb by mass, a molybdenum ion concentration of less than 3,000 ppb by mass, and a zinc ion concentration of less than 1,000 ppb by mass are obtained by feeding crude acetic acid having an iron ion concentration of less than 10,000 ppb by mass, a chromium ion concentration of less than 5,000 ppb by mass, a nickel ion concentration of less than 3,000 ppb by mass, a molybdenum ion concentration of less than 2,000 ppb by mass, a zinc ion concentration of less than 1,000 ppb by mass, a hexyl iodide concentration of less than 510 ppb by mass, and an acetic acid concentration of not less than 80% by mass into the charging mixture feeding plate through a charging pipe having a nickel base alloy or zirconium as a material, and conducting distillation at a column top temperature of less than 165° C. and a column bottom temperature of less than 175° C.

Hereinafter, one embodiment of the present invention will be described. FIG. 1 is one example of an acetic acid production flow diagram (carbonylation process of a methanol method) showing one embodiment of the present invention. An acetic acid production apparatus associated with this acetic acid production flow has a reaction vessel 1, an evaporator 2, a distillation column 3, a decanter 4, a distillation column 5, a distillation column 6, an ion exchange resin column 7, a scrubber system 8, an acetaldehyde separation and removal system 9, condensers 1a, 2a, 3a, 5a, and 6a, a heat exchanger 2b, reboilers 3b, 5b, and 6b, lines 11 to 56, and a pump 57 and is configured to be capable of continuously producing acetic acid. In the method for producing acetic acid according to the present embodiment, a reaction step, an evaporation step (flash step), a first distillation step, a second distillation step, a third distillation step, and an adsorptive removal step are performed in the reaction vessel 1, the evaporator 2, the distillation column 3, the distillation column 5, the distillation column 6, and the ion exchange resin column 7, respectively. The first distillation step is also referred to as a lower boiling point component removal step, the second distillation step is also referred to as a dehydration step, and the third distillation step is also referred to as a higher boiling point component removal step. In the present invention, the steps are not limited to those described above and may exclude, particularly, equipment of the acetaldehyde separation and removal system 9 (acetaldehyde removal column, etc.). As mentioned later, a product column may be disposed downstream of the ion exchange resin column 7.

The reaction vessel 1 is a unit for performing the reaction step. This reaction step is a step for continuously producing acetic acid through a reaction (methanol carbonylation reaction) represented by the chemical formula (1) given below. In a steady operation state of the acetic acid production apparatus, for example, a reaction mixture under stirring with a stirrer is present in the reaction vessel 1. The reaction mixture contains methanol and carbon monoxide which are raw materials, a metal catalyst, a co-catalyst, water, a production target acetic acid, and various by-products, and a liquid phase and a gaseous phase are in equilibrium.

$$CH_3OH + CO \rightarrow CH_3COOH \qquad (1)$$

The raw materials in the reaction mixture are methanol in a liquid state and carbon monoxide in a gaseous state. Methanol is continuously fed at a predetermined flow rate to the reaction vessel 1 from a methanol reservoir (not shown) through the line 11. As described above, the methanol that is distributed on the market often contains zinc. This zinc is also a factor in reducing the life of the silver-substituted ion exchange resin (IER) used in the subsequent adsorptive removal step. Therefore, regarding methanol that contains a large amount of zinc, it is preferred that before such methanol be used in the reaction, the zinc ion concentration in the methanol is reduced by treating the methanol with a cation exchange resin in advance.

Carbon monoxide is continuously fed at a predetermined flow rate to the reaction vessel 1 from a carbon monoxide reservoir (not shown) through the line 12. The carbon monoxide is not necessarily required to be pure carbon monoxide and may contain, for example, other gases such as nitrogen, hydrogen, carbon dioxide, and oxygen, in a small amount (e.g., not more than 5% by mass, preferably not more than 1% by mass).

The metal catalyst in the reaction mixture promotes the carbonylation reaction of methanol, and, for example, a rhodium catalyst or an iridium catalyst can be used. For example, a rhodium complex represented by the chemical formula $[Rh(CO)_2I_2]^-$ can be used as the rhodium catalyst. For example, an iridium complex represented by the chemical formula $[Ir(CO)_2I_2]^-$ can be used as the iridium catalyst. A metal complex catalyst is preferred as the metal catalyst. The concentration (in terms of the metal) of the catalyst in the reaction mixture is, for example, 200 to 5000 ppm by mass, preferably 400 to 2000 ppm by mass, with respect to the whole liquid phase of the reaction mixture.

The co-catalyst is an iodide for assisting the action of the catalyst mentioned above, and, for example, methyl iodide or an ionic iodide is used. The methyl iodide can exhibit the effect of promoting the catalytic effect of the catalyst mentioned above. The concentration of the methyl iodide is, for example, 1 to 20% by mass with respect to the whole liquid phase of the reaction mixture. The ionic iodide is an iodide that generates iodide ions in a reaction solution (particularly, an ionic metal iodide) and can exhibit the effect of stabilizing the catalyst mentioned above and the effect of suppressing side reaction. Examples of the ionic iodide include alkali metal iodides such as lithium iodide, sodium iodide, and potassium iodide. The concentration of the ionic iodide in the reaction mixture is, for example, 1 to 25% by mass, preferably 5 to 20% by mass, with respect to the whole liquid phase of the reaction mixture. Further, for example, when an iridium catalyst and the like are used, as a co-catalyst, a ruthenium compound or an osmium compound may also be used. The amount of such compounds used is, in total, for example, with respect to one mole of iridium (in terms of the metal), 0.1 to 30 moles (in terms of the metal), and is preferably 0.5 to 15 moles (in terms of the metal).

Water in the reaction mixture is a component necessary for generating acetic acid in the reaction mechanism of the methanol carbonylation reaction and is also a component necessary for solubilizing a water-soluble component in the reaction system. The concentration of water in the reaction mixture is, for example, 0.1 to 15% by mass, preferably 0.8 to 10% by mass, further preferably 1 to 6% by mass, particularly preferably 1.5 to 4% by mass, with respect to the whole liquid phase of the reaction mixture. The water concentration is preferably not more than 15% by mass for pursuing efficient acetic acid production by reducing energy required for the removal of water in the course of purification of acetic acid. In order to control the water concentration, water may be continuously fed at a predetermined flow rate to the reaction vessel 1.

The acetic acid in the reaction mixture includes acetic acid fed in advance into the reaction vessel 1 before operation of the acetic acid production apparatus, and acetic acid generated as a main product of the methanol carbonylation reaction. Such acetic acid can function as a solvent in the reaction system. The concentration of the acetic acid in the reaction mixture is, for example, 50 to 90% by mass, preferably 60 to 80% by mass, with respect to the whole liquid phase of the reaction mixture.

Examples of the main by-products contained in the reaction mixture include methyl acetate. This methyl acetate may be generated through the reaction between acetic acid and methanol. The concentration of the methyl acetate in the reaction mixture is, for example, 0.1 to 30% by mass, preferably 1 to 10% by mass, with respect to the whole liquid phase of the reaction mixture. Another example of the by-products contained in the reaction mixture includes hydrogen iodide. This hydrogen iodide is inevitably generated under the reaction mechanism of the methanol carbonylation reaction in the case where the catalyst or the co-catalyst as mentioned above is used. The concentration of the hydrogen iodide in the reaction mixture is, for example, 0.01 to 2% by mass with respect to the whole liquid phase of the reaction mixture. Other examples of the by-products include hydrogen, methane, carbon dioxide, acetaldehyde, crotonaldehyde, 2-ethyl crotonaldehyde, dimethyl ether, alkanes, formic acid, and propionic acid, and alkyl iodides such as ethyl iodide, propyl iodide, butyl iodide, hexyl iodide and decyl iodide. The concentration of hexyl iodide is, for example, 0.1 to 10,000 ppb by mass, normally 0.5 to 1,000 ppb by mass, and often 1 to 100 ppb by mass (e.g., 2 to 50 ppb by mass) with respect to the whole liquid phase of the reaction mixture. Also, the reaction mixture may contain a metal, such as iron, nickel, chromium, manganese, or molybdenum, generated by the corrosion of the apparatus (corroded metal), and other metals such as cobalt, zinc, and copper. The corroded metal and other metals are also collectively referred to as a "corroded metal, etc.".

In the reaction vessel 1 where the reaction mixture as described above is present, the reaction temperature is set to, for example, 150 to 250° C. The reaction pressure as the total pressure is set to, for example, 2.0 to 3.5 MPa (absolute pressure), and the carbon monoxide partial pressure is set to, for example, 0.4 to 1.8 MPa (absolute pressure), preferably 0.6 to 1.6 MPa (absolute pressure), and further preferably 0.9 to 1.4 MPa (absolute pressure).

The vapor of a gaseous phase portion in the reaction vessel 1 during apparatus operation contains, for example, carbon monoxide, hydrogen, methane, carbon dioxide, nitrogen, oxygen, methyl iodide, hydrogen iodide, water, methyl acetate, acetic acid, dimethyl ether, methanol, acetaldehyde, formic acid, and propionic acid. This vapor can be withdrawn from the reaction vessel 1 through the line 13. The internal pressure of the reaction vessel 1 can be controlled by the adjustment of the amount of the vapor withdrawn, and, for example, the internal pressure of the reaction vessel 1 is kept constant. The vapor withdrawn from the reaction vessel 1 is introduced to the condenser 1a.

The condenser 1a separates the vapor from the reaction vessel 1 into a condensate portion and a gaseous portion by cooling and partial condensation. The condensate portion contains, for example, methyl iodide, hydrogen iodide, water, methyl acetate, acetic acid, dimethyl ether, methanol, acetaldehyde, formic acid, and propionic acid and is introduced to the reaction vessel 1 from the condenser 1a through the line 14 and recycled. The gaseous portion contains, for example, carbon monoxide, hydrogen, methane, carbon dioxide, nitrogen, oxygen, methyl iodide, hydrogen iodide, water, methyl acetate, acetic acid, dimethyl ether, methanol, acetaldehyde, and formic acid and is fed to the scrubber system 8 from the condenser 1a through the line 15. In the scrubber system 8, useful components (e.g., methyl iodide, water, methyl acetate, and acetic acid) are separated and recovered from the gaseous portion from the condenser 1a.

In this separation and recovery, a wet method that is performed using an absorbing liquid for capturing the useful components in the gaseous portion is utilized in the present embodiment. An absorption solvent containing at least acetic acid and/or methanol is preferred as the absorbing liquid. The absorbing liquid may contain methyl acetate. For example, a condensate portion of a vapor from the distillation column 6 mentioned later can be used as the absorbing liquid. In the separation and recovery, a pressure swing adsorption method may be used. The separated and recovered useful components (e.g., methyl iodide) are introduced to the reaction vessel 1 from the scrubber system 8 through the recycle line 48 and recycled. A gas after the capturing of the useful components is discarded through the line 49. The gas discharged from the line 49 can be used as a CO source to be introduced to the bottom part of the evaporator 2 mentioned later or the residual liquid stream recycle lines 18 and 19. As for treatment in the scrubber system 8 and subsequent recycle to the reaction vessel 1 and discarding, the same holds true for gaseous portions described later that are fed to the scrubber system 8 from other condensers. For the production method of the present invention, it is preferred to have a scrubber step of separating offgas from the process into a stream rich in carbon monoxide and a stream rich in acetic acid by absorption treatment with an absorption solvent containing at least acetic acid.

In the reaction vessel 1 during apparatus operation, as mentioned above, acetic acid is continuously produced. The reaction mixture containing such acetic acid is continuously withdrawn at a predetermined flow rate from the reaction vessel 1 and introduced to the next evaporator 2 through the line 16.

The evaporator 2 is a unit for performing the evaporation step (flash step). This evaporation step is a step for separating the reaction mixture continuously introduced to the evaporator 2 through the line 16 (reaction mixture feed line), into a vapor stream (volatile phase) and a residual liquid stream (low volatile phase) by partial evaporation. The evaporation may be caused by reducing the pressure without heating the reaction mixture, or the evaporation may be caused by reducing the pressure while heating the reaction mixture. In the evaporation step, the temperature of the vapor stream is, for example, 100 to 260° C., preferably 120 to 200° C., and the temperature of the residual liquid stream is, for example, 80 to 200° C., preferably 100 to 180° C. The internal pressure of the evaporator is, for example, 50 to 1000 kPa (absolute pressure). The ratio between the vapor stream and the residual liquid stream to be separated in the evaporation step is, for example, 10/90 to 50/50 (vapor stream/residual liquid stream) in terms of a mass ratio. The vapor generated in this step contains, for example, methyl iodide, hydrogen iodide, water, methyl acetate, acetic acid, dimethyl ether, methanol, acetaldehyde, formic acid, propionic acid, and alkyl iodides such as ethyl iodide, propyl iodide, butyl iodide, hexyl iodide and decyl iodide and is continuously withdrawn to the line 17 (vapor stream discharge line) from the evaporator 2. A portion of the vapor stream withdrawn from the evaporator 2 is continuously introduced to the condenser 2a, and another portion of the vapor stream is continuously introduced to the next distillation column 3 through the line 21. The acetic acid concentration in the vapor stream is, for example, 50 to 85% by mass, and preferably 55 to 75% by mass, the methyl iodide concentration is, for example, 2 to 50% by mass (preferably 5 to 30% by mass), the water concentration is, for example, 0.2 to 20% by mass (preferably 1 to 15% by mass), and the methyl acetate concentration is, for example, 0.2 to 50% by mass (preferably 2 to 30% by mass). The hexyl iodide concentration in the vapor stream is, for example, 0.1 to 10,000 ppb by mass, normally 0.5 to 1,000 ppb by mass, and often 1 to 100 ppb by mass (e.g., 2 to 50 ppb by mass). The residual liquid stream generated in this step contains, for example, the catalyst and the co-catalyst (methyl iodide, lithium iodide, etc.) contained in the reaction mixture, and water, methyl acetate, acetic acid, formic acid, and propionic acid remaining without being volatilized in this step, and is continuously introduced to the heat exchanger 2b from the evaporator 2 through the line 18 using the pump 57. The heat exchanger 2b cools the residual liquid stream from the evaporator 2. The cooled residual liquid stream is continuously introduced to the reaction vessel 1 from the heat exchanger 2b through the line 19 and recycled. The line 18 and the line 19 are collectively referred to as residual liquid stream recycle lines. The acetic acid concentration of the residual liquid stream is, for example, 55 to 90% by mass, preferably 60 to 85% by mass.

The condenser 2a separates the vapor stream from the evaporator 2 into a condensate portion and a gaseous portion by cooling and partial condensation. The condensate portion contains, for example, methyl iodide, hydrogen iodide, water, methyl acetate, acetic acid, dimethyl ether, methanol, acetaldehyde, formic acid, and propionic acid and is introduced to the reaction vessel 1 from the condenser 2a through the lines 22 and 23 and recycled. The gaseous portion contains, for example, carbon monoxide, hydrogen, methane, carbon dioxide, nitrogen, oxygen, methyl iodide, hydrogen iodide, water, methyl acetate, acetic acid, dimethyl ether, methanol, acetaldehyde, and formic acid and is fed to the scrubber system 8 from the condenser 2a through the lines 20 and 15. Since the reaction to produce acetic acid in the reaction step mentioned above is an exothermic reaction, a portion of heat accumulated in the reaction mixture is transferred to the vapor generated from the reaction mixture in the evaporation step (flash step). The condensate portion generated by the cooling of this vapor in the condenser 2a is recycled to the reaction vessel 1. Specifically, in this acetic acid production apparatus, heat generated through the methanol carbonylation reaction is efficiently removed in the condenser 2a.

The distillation column 3 is a unit for performing the first distillation step and serves as the so-called lower boiling point component removal column in the present embodiment. The first distillation step is the step of subjecting the vapor stream continuously introduced to the distillation column 3 to distillation treatment to separate and remove lower boiling point components. More specifically, in the first distillation step, the vapor stream is separated by distillation into an overhead stream rich in at least one lower boiling point component selected from methyl iodide and acetaldehyde, and an acetic acid stream rich in acetic acid. The distillation column 3 consists of, for example, a distillation column such as a plate column or a packed column. In the case of adopting a plate column as the distillation column 3, the theoretical number of plates thereof is, for example, 5 to 50, and the reflux ratio is, for example, 0.5 to 3000 according to the theoretical number of plates. In the inside of the distillation column 3, the column top pressure is set to, for example, 80 to 160 kPa (gauge pressure), and the column bottom pressure is higher than the column top pressure and is set to, for example, 85 to 180 kPa (gauge pressure). In the inside of the distillation column 3, the column top temperature is, for example, a temperature of lower than the boiling point of acetic acid at the set column top pressure and is set to 90 to 130° C., and the column bottom temperature is, for example, a temperature of not less than the boiling point of acetic acid at the set column bottom pressure and is set to 120 to 165° C. (preferably 125 to 160° C.)

The vapor stream from the evaporator 2 is continuously introduced to the distillation column 3 through the line 21. From the column top of the distillation column 3, a vapor as the overhead stream is continuously withdrawn to the line 24. From the column bottom of the distillation column 3, a bottom fraction is continuously withdrawn to the line 25. 3b denotes a reboiler. From the height position between the column top and the column bottom of the distillation column 3, the acetic acid stream (first acetic acid stream; liquid) as a side stream is continuously withdrawn through the line 27.

The vapor withdrawn from the column top of the distillation column 3 contains a larger amount of components having a lower boiling point (lower boiling point components) than that of acetic acid as compared with the bottom fraction and the side stream from the distillation column 3 and contains, for example, methyl iodide, hydrogen iodide, water, methyl acetate, dimethyl ether, methanol, acetaldehyde, and formic acid. This vapor also contains acetic acid. Such a vapor is continuously introduced to the condenser 3a through the line 24.

The condenser 3a separates the vapor from the distillation column 3 into a condensate portion and a gaseous portion by cooling and partial condensation. The condensate portion contains, for example, methyl iodide, hydrogen iodide, water, methyl acetate, acetic acid, dimethyl ether, methanol, acetaldehyde, and formic acid and is continuously introduced to the decanter 4 from the condenser 3a through the line 28. The condensate portion introduced to the decanter 4 is separated into an aqueous phase (upper phase) and an organic phase (methyl iodide phase; lower phase). The aqueous phase contains water and, for example, methyl iodide, hydrogen iodide, methyl acetate, acetic acid, dimethyl ether, methanol, acetaldehyde, and formic acid. The organic phase contains, for example, methyl iodide and, for example, hydrogen iodide, water, methyl acetate, acetic acid, dimethyl ether, methanol, acetaldehyde, and formic acid. In the present embodiment, a portion of the aqueous phase is refluxed to the distillation column 3 through the line 29, and another portion of the aqueous phase is introduced to the reaction vessel 1 through the lines 29, 30, and 23 and recycled. A portion of the organic phase is introduced to the reaction vessel 1 through the lines 31 and 23 and recycled. Another portion of the organic phase and/or a remaining portion of the aqueous phase is introduced to the acetaldehyde separation and removal system 9 through the lines 31 and 50 and/or the lines 30 and 51.

In the acetaldehyde separation and removal step using the acetaldehyde separation and removal system 9, acetaldehyde contained in the organic phase and/or the aqueous phase is separated and removed by a method known in the art, for example, distillation, extraction, or a combination thereof. The separated acetaldehyde is discharge to the outside of the apparatus through the line 53. The useful components (e.g., methyl iodide) contained in the organic phase and/or the aqueous phase are recycled to the reaction vessel 1 through the lines 52 and 23 and reused.

FIG. 2 is a schematic flow diagram showing one example of the acetaldehyde separation and removal system. According to this flow, in the case of treating, for example, the organic phase in the acetaldehyde separation and removal step, the organic phase is fed to a distillation column (first acetaldehyde removal column) 91 through a line 101 and separated by distillation into an overhead stream rich in acetaldehyde (line 102) and a residual liquid stream rich in methyl iodide (line 103). The overhead stream is condensed in a condenser 91a. A portion of the condensate is refluxed to the column top of the distillation column 91 (line 104), and the remaining portion of the condensate is fed to an extraction column 92 (line 105). The condensate fed to the extraction column 92 is subjected to extraction treatment with water introduced from a line 109. The extract obtained by the extraction treatment is fed to a distillation column (second acetaldehyde removal column) 93 through a line 107 and separated by distillation into an overhead stream rich in acetaldehyde (line 112) and a residual liquid stream rich in water (line 113). Then, the overhead stream rich in acetaldehyde is condensed in a condenser 93a. A portion of the condensate is refluxed to the column top of the distillation column 93 (line 114), and the remaining portion of the condensate is discharged to the outside of the system (line 115). The residual liquid stream rich in methyl iodide, which is a bottom fraction of the first acetaldehyde removal column 91, a raffinate rich in methyl iodide (line 108) obtained in the extraction column 92, and the residual liquid stream rich in water, which is a bottom fraction of the second acetaldehyde removal column 93 are recycled to the reaction vessel 1 through the lines 103, 111, and 113, respectively, or recycled to an appropriate area of the process and reused. For example, the raffinate rich in methyl iodide, obtained in the extraction column 92, can be recycled to the distillation column 91 through a line 110. The liquid from the line 113 is usually discharged to the outside as water discharge. A gas that has not been condensed in the condenser 91a or 93a (line 106 or 116) is subjected to absorption treatment in the scrubber system 8 or discarded.

According to the flow of FIG. 2, in the case of treating the aqueous phase in the acetaldehyde separation and removal step, for example, the aqueous phase is fed to the distillation column (first acetaldehyde removal column) 91 through the line 101 and separated by distillation into an overhead stream rich in acetaldehyde (line 102) and a residual liquid stream rich in water (line 103). The overhead stream is condensed in the condenser 91a. A portion of the condensate is refluxed to the column top of the distillation column 91 (line 104), and the remaining portion of the condensate is fed to the extraction column 92 (line 105). The condensate fed to the extraction column 92 is subjected to extraction treatment with water introduced from the line 109. The extract obtained by the extraction treatment is fed to the distillation column (second acetaldehyde removal column) 93 through the line 107 and separated by distillation into an overhead stream rich in acetaldehyde (line 112) and a residual liquid stream rich in water (line 113). Then, the overhead stream rich in acetaldehyde is condensed in the condenser 93a. A portion of the condensate is refluxed to the column top of the distillation column 93 (line 114), and the remaining portion of the condensate is discharged to the outside of the system (line 115). The residual liquid stream rich in water, which is a bottom fraction of the first acetaldehyde removal column 91, a raffinate rich in methyl iodide (line 108) obtained in the extraction column 92, and the residual liquid stream rich in water, which is a bottom fraction of the second acetaldehyde removal column 93 are recycled to the reaction vessel 1 through the lines 103, 111, and 113, respectively, or recycled to an appropriate area of the process and reused. For example, the raffinate rich in methyl iodide, obtained in the extraction column 92, can be recycled to the distillation column 91 through the line 110. The liquid from the line 113 is usually discharged to the outside as water discharge. A gas that has not been condensed in the condenser 91a or 93a (line 106 or 116) is subjected to absorption treatment in the scrubber system 8 or discarded.

The acetaldehyde derived from the process stream containing at least the water, the acetic acid (AC), the methyl iodide (MeI), and the acetaldehyde (AD) can also be separated and removed by use of extractive distillation, in addition to the method described above. For example, the organic phase and/or the aqueous phase (charging mixture) obtained by the separation of the process stream is fed to a distillation column (extractive distillation column). In addition, an extraction solvent (usually, water) is introduced to a concentration zone (e.g., space from the column top to the charging mixture feeding position) where methyl iodide and acetaldehyde in the distillation column are concentrated. A liquid (extract) dropped from the concentration zone is withdrawn as a side stream (side cut stream). This side stream is separated into an aqueous phase and an organic phase. The aqueous phase can be distilled to thereby discharge acetaldehyde to the outside of the system. In the case where a relatively large amount of water is present in the distillation column, the liquid dropped from the concentration zone may be withdrawn as a side stream without introducing the extraction solvent to the distillation column. For example, a unit (chimney tray, etc.) that can receive the liquid (extract) dropped from the concentration zone is disposed in this distillation column so that a liquid (extract) received by this unit can be withdrawn as a side stream. The extraction solvent introduction position is preferably superior to the charging mixture feeding position, more preferably near the column top. The side stream withdrawal position is preferably lower than the extraction solvent introduction position and higher than the charging mixture feeding position, in the height direction of the column. According to this method, acetaldehyde can be extracted with a high concentration from a concentrate of methyl iodide and the acetaldehyde using an extraction solvent (usually, water). In addition, the region between the extraction solvent introduction site and the side cut site is used as an extraction zone. Therefore, acetaldehyde can be efficiently extracted with a small amount of the extraction solvent. Therefore, for example, the number of plates in the distillation column can be drastically decreased as compared with a method of withdrawing an extract by extractive distillation from the column bottom of the distillation column (extractive distillation column). In addition, steam load can also be reduced. Furthermore, the ratio of methyl iodide to acetaldehyde (MeI/AD ratio) in a water extract can be decreased as compared with a method of combining the aldehyde removing distillation of FIG. 2 with water extraction using a small amount of an extraction solvent. Therefore, acetaldehyde can be removed under conditions that can suppress a loss of methyl iodide to the outside of the system. The acetaldehyde concentration in the side stream is much higher than the acetaldehyde concentration in the charging mixture and the bottom fraction (column bottom fraction). The ratio of acetaldehyde to methyl iodide in the side stream is larger than the ratio of acetaldehyde to methyl iodide in the charging mixture and the bottom fraction. The organic phase (methyl iodide phase) obtained by the separation of the side stream may be recycled to this distillation column. In this case, the recycle position of the organic phase obtained by the separation of the side stream is preferably lower than the side stream withdrawal position and preferably higher than the charging mixture feeding position, in the height direction of the column. A solvent miscible with the components (e.g., methyl acetate) constituting the organic phase obtained by the separation of the process stream may be introduced to this distillation column (extractive distillation column). Examples of the miscible solvent include acetic acid and ethyl acetate. The miscible solvent introduction position is preferably lower than the side stream withdrawal position and preferably higher than the charging mixture feeding position, in the height direction of the column. Also, the miscible solvent introduction position is preferably inferior to a recycle position in the case where the organic phase obtained by the separation of the side stream is recycled to this distillation column. The organic phase obtained by the separation of the side stream is recycled to the distillation column, or the miscible solvent is introduced to the distillation column, whereby the methyl acetate concentration in the extract withdrawn as the side stream can be decreased, and the methyl acetate concentration in the aqueous phase obtained by the separation of the extract can be lowered. Hence, the contamination of the aqueous phase with methyl iodide can be suppressed.

The theoretical number of plates of the distillation column (extractive distillation column) is, for example, 1 to 100, preferably 2 to 50, further preferably 3 to 30, particularly preferably 5 to 20. Acetaldehyde can be efficiently separated and removed by a smaller number of plates than 80 to 100 plates in a distillation column or an extractive distillation column for use in conventional acetaldehyde removal. The mass ratio between the flow rate of the extraction solvent and the flow rate of the charging mixture (the organic phase and/or the aqueous phase obtained by the separation of the process stream) (former/latter) may be selected from the range of 0.0001/100 to 100/100 and is usually 0.0001/100 to 20/100, preferably 0.001/100 to 10/100, more preferably 0.01/100 to 8/100, further preferably 0.1/100 to 5/100. The column top temperature of the distillation column (extractive distillation column) is, for example, 15 to 120° C., preferably 20 to 90° C., more preferably 20 to 80° C., further preferably 25 to 70° C. The column top pressure is, on the order of, for example, 0.1 to 0.5 MPa in terms of absolute pressure. Other conditions for the distillation column (extractive distillation column) may be the same as those for a distillation column or an extractive distillation column for use in conventional acetaldehyde removal.

FIG. 3 is a schematic flow diagram showing another example of the acetaldehyde separation and removal system using the extractive distillation described above. In this example, the organic phase and/or the aqueous phase (charging mixture) obtained by the separation of the process stream is fed to a middle part (position between the column top and the column bottom) of a distillation column 94 through a feed line 201, while water is introduced thereto from near the column top through a line 202 so that extractive distillation is performed in the distillation column 94 (extractive distillation column). A chimney tray 200 for receiving a liquid (extract) dropped from a concentration zone where methyl iodide and acetaldehyde in the column are concentrated is disposed superior to the charging mixture feeding position of the distillation column 94. In this extractive distillation, preferably the whole amount, of the liquid on the chimney tray 200 is withdrawn, introduced to a decanter 95 through a line 208, and separated. The aqueous phase (containing acetaldehyde) in the decanter 95 is introduced to a cooler 95a through a line 212 and cooled so that methyl iodide dissolved in the aqueous phase is separated into 2 phases in a decanter 96. The aqueous phase in the decanter 96 is fed to a distillation column 97 (acetaldehyde removal column) through a line 216 and distilled. The vapor at the column top is led to a condenser 97a through a line 217 and condensed. A portion of the condensate (mainly, acetaldehyde and methyl iodide) is refluxed to the column top of the distillation column 97, and the remaining portion is discarded or fed to a distillation column 98 (extractive distillation column) through a line 220. Water is introduced thereto from near the column top of the distillation column 98 through a line 222, followed by extractive distillation. The vapor at the column top is led to a condenser 98*a* through a line 223 and condensed. A portion of the condensate (mainly, methyl iodide) is refluxed to the column top, and the remaining portion is recycled to the reaction system through a line 226, but may be discharged to the outside of the system. Preferably the whole amount, of the organic phase (methyl iodide phase) in the decanter 95 is recycled to below the position of the chimney tray 200 of the distillation column 94 through lines 209 and 210. A portion of the aqueous phase of the decanter 95 and the organic phase of the decanter 96 are recycled to the distillation column 94 through lines 213 and 210 and lines 214 and 210, respectively, but may not be recycled. A portion of the aqueous phase of the decanter 95 may be utilized as an extraction solvent (water) in the distillation column 94. A portion of the aqueous phase of the decanter 96 may be recycled to the distillation column 94 through the line 210. In some cases (e.g., the case where methyl acetate is contained in the charging mixture), a solvent (acetic acid, ethyl acetate, etc.) miscible with the components (e.g., methyl acetate) constituting the organic phase obtained by the separation of the process stream may be fed to the distillation column 94 through a line 215 to thereby improve distillation efficiency. The feeding position of the miscible solvent to the distillation column 94 is superior to the charging mixture feeding portion (junction of the line 201) and inferior to the junction of the recycle line 210. A bottom fraction of the distillation column 94 is recycled to the reaction system. A vapor at the column top of the distillation column 94 is led to a condenser 94*a* through a line 203 and condensed. The condensate is separated in a decanter 99. The organic phase is refluxed to the column top of the distillation column 94 through a line 206, while the aqueous phase is led to the decanter 95 through a line 207. A bottom fraction (water is a main component) of the distillation column 97 and a bottom fraction (water containing a small amount of acetaldehyde) of the distillation column 98 (extractive distillation column) are discharged to the outside of the system through lines 218 and 224, respectively, or recycled to the reaction system. A gas that has not been condensed in the condenser 94*a*, 97*a*, or 98*a* (line 211, 221, or 227) is subjected to absorption treatment in the scrubber system 8, or discarded.

FIG. 4 is a schematic flow diagram showing a further alternative example of the acetaldehyde separation and removal system using the extractive distillation described above. In this example, a condensate of a vapor from the column top of the distillation column 94 is led to a hold tank 100, and the whole amount thereof is refluxed to the column top of the distillation column 94 through the line 206. The other points are the same as in the example of FIG. 3.

FIG. 5 is a schematic flow diagram showing a further alternative example of the acetaldehyde separation and removal system using the extractive distillation described above. In this example, the whole amount of a liquid on the chimney tray 200 is withdrawn, directly introduced to the cooler 95*a* through the line 208 without the medium of the decanter 95, cooled, and fed to the decanter 96. The other points are the same as in the example of FIG. 4.

In FIG. 1 described above, the gaseous portion generated in the condenser 3*a* contains, for example, carbon monoxide, hydrogen, methane, carbon dioxide, nitrogen, oxygen, methyl iodide, hydrogen iodide, water, methyl acetate, acetic acid, dimethyl ether, methanol, acetaldehyde, and formic acid and is fed to the scrubber system 8 from the condenser 3*a* through the lines 32 and 15. For example, methyl iodide, hydrogen iodide, water, methyl acetate, acetic acid, dimethyl ether, methanol, acetaldehyde, and formic acid in the gaseous portion that has entered the scrubber system 8 are absorbed to an absorbing liquid in the scrubber system 8. The hydrogen iodide generates methyl iodide through reaction with methanol or methyl acetate in the absorbing liquid. Then, a liquid portion containing useful components such as the methyl iodide is recycled to the reaction vessel 1 from the scrubber system 8 through the recycle lines 48 and 23 and reused.

The bottom fraction withdrawn from the column bottom of the distillation column 3 contains a larger amount of components having a higher boiling point (higher boiling point components) than that of acetic acid as compared with the overhead stream and the side stream from the distillation column 3 and contains, for example, propionic acid, and the entrained catalyst and co-catalyst mentioned above. This bottom fraction also contains, for example, acetic acid, methyl iodide, methyl acetate, and water. In the present embodiment, a portion of such a bottom fraction is continuously introduced to the evaporator 2 through the lines 25 and 26 and recycled, and another portion of the bottom fraction is continuously introduced to the reaction vessel 1 through the lines 25 and 23 and recycled.

The first acetic acid stream continuously withdrawn as a side stream from the distillation column 3 is more enriched with acetic acid than the vapor stream continuously introduced to the distillation column 3. Specifically, the acetic acid concentration of the first acetic acid stream is higher than the acetic acid concentration of the vapor stream. The acetic acid concentration of the first acetic acid stream is, for example, 90 to 99.9% by mass, preferably 93 to 99% by mass. Also, the first acetic acid stream contains, in addition to acetic acid, for example, methyl iodide, hydrogen iodide, water, methyl acetate, dimethyl ether, methanol, acetaldehyde, formic acid, and propionic acid, and alkyl iodides such as ethyl iodide, propyl iodide, butyl iodide, hexyl iodide and decyl iodide. In the first acetic acid stream, the methyl iodide concentration is, for example, 0.1 to 8% by mass, and preferably 0.2 to 5% by mass, the water concentration is, for example, 0.1 to 8% by mass, and preferably 0.2 to 5% by mass, and the methyl acetate concentration is, for example, 0.1 to 8% by mass, and preferably 0.2 to 5% by mass. The hexyl iodide concentration in the first acetic acid stream is, for example, 0.2 to 10,000 ppb by mass, normally 1 to 1,000 ppb by mass, and often 2 to 100 ppb by mass (e.g., 3 to 50 ppb by mass). The connection position of the line 27 to the distillation column 3 may be, as shown in the drawing, higher than the connection position of the line 21 to the distillation column 3 in the height direction of the distillation column 3, but may be lower than the connection position of the line 21 to the distillation column 3 or may be the same as the connection position of the line 21 to the distillation column 3. The first acetic acid stream from the distillation column 3 is continuously introduced at a predetermined flow rate to the next distillation column 5 through the line 27. The material of the line 27 or the material of the distillation column 5 (at least the material of the portions in contact with the liquids and gases) may be stainless steel, but it is preferred that a metal having high corrosion resistance, such as a nickel base alloy and zirconium, be used in order to suppress corrosion of the inner portions of the pipes by hydrogen iodide and acetic acid.

To the first acetic acid stream flowing through the line 27, potassium hydroxide can be fed or added through the line 55 (potassium hydroxide introduction line). The potassium hydroxide can be fed or added, for example, as a solution such as an aqueous solution. Hydrogen iodide in the first acetic acid stream can be decreased by the feed or addition of potassium hydroxide to the first acetic acid stream. Specifically, the hydrogen iodide reacts with the potassium hydroxide to form potassium iodide and water. This can reduce the corrosion of an apparatus such as a distillation column ascribable to hydrogen iodide. In this process, the potassium hydroxide can be fed or added to an appropriate site where hydrogen iodide is present. The potassium hydroxide added during the process also reacts with acetic acid to form potassium acetate.

The distillation column 5 is a unit for performing the second distillation step and serves as the so-called dehydration column in the present embodiment. The second distillation step is a step for further purifying acetic acid by the distillation treatment of the first acetic acid stream continuously introduced to the distillation column 5. In the present invention, the material of the distillation column 5 (at least the material of the liquid contact part and the gas contact part) is a nickel base alloy or zirconium. By using such a material, corrosion of the inner portions of the distillation column by hydrogen iodide and acetic acid can be suppressed, and elution of corroded metal ions can also be suppressed.

The charging mixture of the distillation column 5 includes at least a part (line 27) of the first acetic acid stream, to which a stream other than the first acetic acid stream [e.g., a recycle stream from a downstream step (e.g., line 42)] may be added. In the present invention, as the metal ion concentrations in the charging mixture of the distillation column 5, the iron ion concentration is less than 10,000 ppb by mass, the chromium ion concentration is less than 5,000 ppb by mass, the nickel ion concentration is less than 3,000 ppb by mass, and the molybdenum ion concentration is less than 2,000 ppb by mass. By employing the above-described specific material for the material of the distillation column 5, and controlling the metal ion concentrations in the charging mixture to the distillation column 5 within the above-described ranges, the corroded metal concentrations in the purified acetic acid obtained in this step can be remarkably reduced, the metal concentrations in the acetic acid fed to the subsequent adsorptive removal step can also be reduced, and the life of the silver-substituted ion exchange resin (IER) can be greatly improved. It is preferred that the iron ion concentration in the charging mixture of the distillation column 5 be less than 9,000 ppb by mass, more preferably less than 5,000 ppb by mass, further preferably less than 3,000 ppb by mass, particularly preferably less than 1,500 ppb by mass, and especially less than 800 ppb by mass (e.g., less than 400 ppb by mass). It is preferred that the chromium ion concentration in the charging mixture be less than 4,000 ppb by mass, more preferably less than 2,500 ppb by mass, further preferably less than 1,500 ppb by mass, particularly preferably less than 750 ppb by mass, and especially less than 400 ppb by mass (e.g., less than 200 ppb by mass). It is preferred that the nickel ion concentration in the charging mixture be less than 2,500 ppb by mass, more preferably less than 2,000 ppb by mass, further preferably less than 1,000 ppb by mass, particularly preferably less than 500 ppb by mass, and especially less than 250 ppb by mass (e.g., less than 150 ppb by mass). It is preferred that the molybdenum ion concentration in the charging mixture be less than 1,700 ppb by mass, more preferably less than 1,200 ppb by mass, further preferably less than 700 ppb by mass, particularly preferably less than 350 ppb by mass, and especially less than 170 ppb by mass. Further, the zinc ion concentration in the charging mixture is, for example, less than 1,000 ppb by mass, preferably less than 800 ppb by mass, more preferably less than 650 ppb by mass, further preferably less than 500 ppb by mass, particularly preferably less than 410 ppb by mass, and especially less than 200 ppb by mass. The hexyl iodide concentration in the charging mixture is, for example, 0.2 to 10,000 ppb by mass, normally 1 to 1,000 ppb by mass, and often 2 to 100 ppb by mass (e.g., 3 to 50 ppb by mass, and particularly 5 to 40 ppb by mass).

The distillation column 5 consists of, for example, a distillation column such as a plate column and a packed column. In the case of adopting a plate column as the distillation column 5, the theoretical number of plates thereof is, for example, 5 to 50, and the reflux ratio is, for example, 0.2 to 3,000 according to the theoretical number of plates.

In the inside of the distillation column 5 that is at the second distillation step, the column top pressure is set to, for example, 0.10 to 0.28 MPa (gauge pressure), preferably 0.15 to 0.23 MPa (gauge pressure), and further preferably 0.17 to 0.21 MPa (gauge pressure). The column bottom pressure is higher than the column top pressure, and is set to, for example, 0.13 to 0.31 MPa (gauge pressure), preferably 0.18 to 0.26 MPa (gauge pressure), and further preferably 0.20 to 0.24 MPa (gauge pressure). In the inside of the distillation column 5 that is at the second distillation step, it is preferred that the column top temperature be less than 165° C., and column bottom temperature be less than 175° C. By setting the column top temperature and the column bottom temperature of the dehydration column in the above-described ranges, corrosion of the inner portions of the distillation column by hydrogen iodide and acetic acid can be suppressed more, and elution of corroded metal ions can also be suppressed more. It is more preferred that the column top temperature be less than 163° C., further preferably less than 161° C., particularly preferably less than 160° C., and especially preferably less than 155° C. The lower limit of the column top temperature is, for example, 110° C. It is more preferred that the column bottom temperature be less than 173° C., further preferably less than 171° C., and particularly preferably less than 166° C. The lower limit of the column bottom temperature is, for example, 120° C.

In order to achieve a sufficient concentration and separation efficiency of water in the dehydration column, it is preferred that the plate spacing (number of plates) between the charging mixture feeding plate (feeding plate) and the column top vapor withdrawal plate of the dehydration column be, in terms of actual plates, not less than 1 plate, more preferably not less than 3 plates, further preferably not less than 5 plates, and particularly preferably not less than 8 plates (among other things, not less than 10 plates).

A vapor as an overhead stream is continuously withdrawn to the line 33 from the column top of the distillation column 5. A bottom fraction is continuously withdrawn to the line 34 from the column bottom of the distillation column 5. 5b denotes a reboiler. A side stream (liquid or gas) may be continuously withdrawn to the line 34 from the height position between the column top and the column bottom of the distillation column 5.

The vapor withdrawn from the column top of the distillation column 5 contains a larger amount of components having a lower boiling point (lower boiling point components) than that of acetic acid as compared with the bottom fraction from the distillation column 5 and contains, for example, methyl iodide, hydrogen iodide, water, methyl acetate, acetic acid, dimethyl ether, methanol, acetaldehyde, and formic acid. Such a vapor is continuously introduced to the condenser 5a through the line 33.

The condenser 5a separates the vapor from the distillation column 5 into a condensate portion and a gaseous portion by cooling and partial condensation. The condensate portion contains, for example, water and acetic acid. A portion of the condensate portion is continuously refluxed to the distillation column 5 from the condenser 5a through the line 35. Another portion of the condensate portion is continuously introduced to the reaction vessel 1 from the condenser 5a through the lines 35, 36, and 23 and recycled. The gaseous portion generated in the condenser 5a contains, for example, carbon monoxide, hydrogen, methane, carbon dioxide, nitrogen, oxygen, methyl iodide, hydrogen iodide, water, methyl acetate, acetic acid, dimethyl ether, methanol, acetaldehyde, and formic acid and is fed to the scrubber system 8 from the condenser 5a through the lines 37 and 15. Hydrogen iodide in the gaseous portion that has entered the scrubber system 8 is absorbed to an absorbing liquid in the scrubber system 8. Methyl iodide is generated through the reaction of the hydrogen iodide with methanol or methyl acetate in the absorbing liquid. Then, a liquid portion containing useful components such as the methyl iodide is recycled to the reaction vessel 1 from the scrubber system 8 through the recycle lines 48 and 23 and reused.

The bottom fraction (or the side stream) withdrawn from the column bottom of the distillation column 5 contains a larger amount of components having a higher boiling point (higher boiling point components) than that of acetic acid as compared with the overhead stream from the distillation column 5 and contains, for example, propionic acid, potassium acetate (in the case of feeding potassium hydroxide to the line 27, etc.), and the entrained catalyst and co-catalyst mentioned above. This bottom fraction may also contain acetic acid. Such a bottom fraction is continuously introduced in the form of the second acetic acid stream to the next distillation column 6 through the line 34.

The second acetic acid stream is more enriched with acetic acid than the first acetic acid stream continuously introduced to the distillation column 5. Specifically, the acetic acid concentration of the second acetic acid stream is higher than the acetic acid concentration of the first acetic acid stream. The acetic acid concentration of the second acetic acid stream is, for example, 99.1 to 99.99% by mass as long as being higher than the acetic acid concentration of the first acetic acid stream. Also, the second acetic acid stream may contain, as described above, in addition to acetic acid, for example, propionic acid and hydrogen iodide. In the present embodiment, in the case of withdrawing a side stream, the withdrawal position of the side stream from the distillation column 5 is lower than the introduction position of the first acetic acid stream to the distillation column 5 in the height direction of the distillation column 5.

In the present invention, because a specific material is employed for the material of the dehydration column, and the metal ion concentrations in the dehydration column charging mixture are not more than certain values, the metal ion concentrations in the second acetic acid steam, which is obtained as a side stream or a bottom stream of the dehydration column, can be remarkably reduced. The iron ion concentration in the second acetic acid stream is, for example, is less than 21,000 ppb by mass, preferably less than 16,000 ppb by mass, more preferably less than 6,000 ppb by mass, further preferably less than 2,000 ppb by mass, and particularly preferably less than 200 ppb by mass. The chromium ion concentration in the second acetic acid stream is, for example, less than 7,100 ppb by mass, preferably less than 5,000 ppb by mass, more preferably less than 3,000 ppb by mass, further preferably less than 1,000 ppb by mass, and particularly preferably less than 100 ppb by mass. The nickel ion concentration in the second acetic acid stream is, for example, less than 4,000 ppb by mass, preferably less than 3,000 ppb by mass, more preferably less than 1,800 ppb by mass, further preferably less than 700 ppb by mass, and particularly preferably less than 70 ppb by mass. The molybdenum ion concentration in the second acetic acid stream is, for example, less than 3,000 ppb by mass, preferably less than 2,500 ppb by mass, more preferably less than 1,500 ppb by mass, further preferably less than 500 ppb by mass, and particularly preferably less than 50 ppb by mass. The zinc ion concentration in the second acetic acid stream is, for example, less than 1,000 ppb by mass, preferably less than 850 ppb by mass, more preferably less than 710 ppb by mass, further preferably less than 410 ppb by mass, and particularly preferably less than 150 ppb by mass. The hexyl iodide concentration in the second acetic acid stream is, for example, 0.2 to 10,000 ppb by mass, normally 1 to 1,000 ppb by mass, and often 2 to 100 ppb by mass (e.g., 3 to 50 ppb by mass, and particularly 5 to 40 ppb by mass).

To the second acetic acid stream flowing through the line 34, potassium hydroxide can be fed or added through the line 56 (potassium hydroxide introduction line). The potassium hydroxide can be fed or added, for example, as a solution such as an aqueous solution. Hydrogen iodide in the second acetic acid stream can be decreased by the feed or addition of potassium hydroxide to the second acetic acid stream. Specifically, the hydrogen iodide reacts with the potassium hydroxide to form potassium iodide and water. This can reduce the corrosion of an apparatus such as a distillation column ascribable to hydrogen iodide.

The distillation column 6 is a unit for performing the third distillation step and serves as the so-called higher boiling point component removal column in the present embodiment. The third distillation step is a step for further purifying acetic acid by the purification treatment of the second acetic acid stream continuously introduced to the distillation column 6. The distillation column 6 consists of, for example, a distillation column such as a plate column or a packed column. In the case of adopting a plate column as the distillation column 6, the theoretical number of plates thereof is, for example, 5 to 50, and the reflux ratio is, for example, 0.2 to 3000 according to the theoretical number of plates. In the inside of the distillation column 6 in the third distillation step, the column top pressure is set to, for example, −100 to 150 kPa (gauge pressure), and the column bottom pressure is higher than the column top pressure and is set to, for example, −90 to 180 kPa (gauge pressure). In the inside of the distillation column 6 in the third distillation step, the column top temperature is, for example, a temperature of higher than the boiling point of water and lower than the boiling point of acetic acid at the set column top pressure and is set to 50 to 150° C., and the column bottom temperature is, for example, a temperature of higher than the boiling point of acetic acid at the set column bottom pressure and is set to 70 to 160° C.

A vapor as an overhead stream is continuously withdrawn to the line 38 from the column top of the distillation column 6. A bottom fraction is continuously withdrawn to the line 39 from the column bottom of the distillation column 6. 6b denotes a reboiler. A side stream (liquid or gas) is continuously withdrawn to the line 46 from the height position between the column top and the column bottom of the distillation column 6. The connection position of the line 46 to the distillation column 6 may be, as shown in the drawing, higher than the connection position of the line 34 to the distillation column 6 in the height direction of the distillation column 6, but may be lower than the connection position of the line 34 to the distillation column 6 or may be the same as the connection position of the line 34 to the distillation column 6.

The vapor withdrawn from the column top of the distillation column 6 contains a larger amount of components having a lower boiling point (lower boiling point components) than that of acetic acid as compared with the bottom fraction from the distillation column 6 and contains, in addition to acetic acid, for example, methyl iodide, hydrogen iodide, water, methyl acetate, dimethyl ether, methanol, and formic acid. Such a vapor is continuously introduced to the condenser 6a through the line 38.

The condenser 6a separates the vapor from the distillation column 6 into a condensate portion and a gaseous portion by cooling and partial condensation. The condensate portion contains, in addition to acetic acid, for example, methyl iodide, hydrogen iodide, water, methyl acetate, dimethyl ether, methanol, and formic acid. At least a portion of the condensate portion is continuously refluxed to the distillation column 6 from the condenser 6a through the line 40. A portion (distillate) of the condensate portion may be recycled to the first acetic acid stream in the line 27 before introduction to the distillation column 5 from the condenser 6a through the lines 40, 41, and 42. Together with this or instead of this, a portion (distillate) of the condensate portion may be recycled to the vapor stream in the line 21 before introduction to the distillation column 3 from the condenser 6a through the lines 40, 41, and 43. Also, a portion (distillate) of the condensate portion may be recycled to the reaction vessel 1 from the condenser 6a through the lines 40, 44, and 23. Furthermore, as mentioned above, a portion of the distillate from the condenser 6a may be fed to the scrubber system 8 and used as an absorbing liquid in this system. In the scrubber system 8, a gaseous portion after absorption of a useful portion is discharged to the outside of the apparatus. Then, a liquid portion containing the useful components is introduced or recycled to the reaction vessel 1 from the scrubber system 8 through the recycle lines 48 and 23 and reused. In addition, a portion of the distillate from the condenser 6a may be led to various pumps (not shown) operated in the apparatus, through lines (not shown) and used as sealing solutions in these pumps. In addition, a portion of the distillate from the condenser 6a may be steadily withdrawn to the outside of the apparatus through a withdrawal line attached to the line 40, or may be non-steadily withdrawn to the outside of the apparatus when needed. In the case where a portion (distillate) of the condensate portion is removed from the distillation treatment system in the distillation column 6, the amount of the distillate (ratio of the distillate) is, for example, 0.01 to 30% by mass, preferably 0.1 to 10% by mass, more preferably 0.3 to 5% by mass, more preferably 0.5 to 3% by mass, of the condensate generated in the condenser 6a. On the other hand, the gaseous portion generated in the condenser 6a contains, for example, carbon monoxide, hydrogen, methane, carbon dioxide, nitrogen, oxygen, methyl iodide, hydrogen iodide, water, methyl acetate, acetic acid, dimethyl ether, methanol, acetaldehyde, and formic acid and is fed to the scrubber system 8 from the condenser 6a through the lines 45 and 15.

The bottom fraction withdrawn from the column bottom of the distillation column 6 through the line 39 contains a larger amount of components having a higher boiling point (higher boiling point components) than that of acetic acid as compared with the overhead stream from the distillation column 6 and contains, for example, propionic acid and acetate such as potassium acetate (in the case of feeding alkali such as potassium hydroxide to the line 34, etc.). Also, the bottom fraction withdrawn from the column bottom of the distillation column 6 through the line 39 also contains, for example, a corroded metal such as a metal formed at and released from the inside wall of a member constituting this acetic acid production apparatus, and a compound of iodine derived from corrosive iodine and the corroded metal, etc. In the present embodiment, such a bottom fraction is discharged to the outside of the acetic acid production apparatus.

The side stream continuously withdrawn to the line 46 from the distillation column 6 is continuously introduced as a third acetic acid stream to the next ion exchange resin column 7. This third acetic acid stream is more enriched with acetic acid than the second acetic acid stream continuously introduced to the distillation column 6. Specifically, the acetic acid concentration of the third acetic acid stream is higher than the acetic acid concentration of the second acetic acid stream. The acetic acid concentration of the third acetic acid stream is, for example, 99.8 to 99.999% by mass as long as being higher than the acetic acid concentration of the second acetic acid stream. The hexyl iodide concentration in the third acetic acid stream is, for example, 0.2 to 10,000 ppb by mass, normally 1 to 1,000 ppb by mass, and often 2 to 100 ppb by mass (e.g., 3 to 50 ppb by mass, and particularly 5 to 40 ppb by mass). In the present embodiment, the withdrawal position of the side stream from the distillation column 6 is higher than the introduction position of the second acetic acid stream to the distillation column 6 in the height direction of the distillation column 6. In another embodiment, the withdrawal position of the side stream from the distillation column 6 is the same as or lower than the introduction position of the second acetic acid stream to the distillation column 6 in the height direction of the distillation column 6. A simple distillator (evaporator) may be used in place of the distillation column 6. Also, the distillation column 6 can be omitted as long as the removal of impurities in the distillation column 5 is adequately performed.

The ion exchange resin column 7 is a purification unit for performing the adsorptive removal step. This adsorptive removal step is a step for further purifying acetic acid by the adsorptive removal of, mainly, alkyl iodides (e.g., ethyl iodide, propyl iodide, butyl iodide, hexyl iodide, and decyl iodide) contained in a very small amount in the third acetic acid stream continuously introduced to the ion exchange resin column 7. In the ion exchange resin column 7, an ion exchange resin having the ability to adsorb alkyl iodides is packed in the column to establish an ion exchange resin bed. Examples of such an ion exchange resin can include cation exchange resins in which a portion of leaving protons in an exchange group such as a sulfonic acid group, a carboxyl group, or a phosphonic acid group is substituted by a metal such as silver or copper. In the adsorptive removal step, for example, the third acetic acid stream (liquid) flows through the inside of the ion exchange resin column 7 packed with such an ion exchange resin, and in the course of this flow, impurities such as the alkyl iodides in the third acetic acid stream are adsorbed to the ion exchange resin and removed from the third acetic acid stream. In the ion exchange resin column 7 in the adsorptive removal step, the internal temperature is, for example, 18 to 100° C., and the rate of the acetic acid stream [the throughput of acetic acid per m³ resin volume (m³/h)] is, for example, 3 to 15 m³/h·m³ (resin volume).

A fourth acetic acid stream is continuously led to the line 47 from the lower end of the ion exchange resin column 7. The acetic acid concentration of the fourth acetic acid stream is higher than the acetic acid concentration of the third acetic acid stream. Specifically, the fourth acetic acid stream is more enriched with acetic acid than the third acetic acid stream continuously introduced to the ion exchange resin column 7. The acetic acid concentration of the fourth acetic acid stream is, for example, 99.9 to 99.999% by mass or not less than this range as long as being higher than the acetic acid concentration of the third acetic acid stream. The hexyl iodide concentration in the fourth acetic acid stream is normally not more than 1 ppb by mass, but may be, for example, 0 to 30 ppb by mass, and particularly 0.01 to 10 ppb by mass (e.g., 0.1 to 5 ppb by mass). In this production method, this fourth acetic acid stream can be retained in a product tank (not shown).

In this acetic acid production apparatus, a so-called product column or finishing column which is a distillation column may be disposed as a purification unit for further purifying the fourth acetic acid stream from the ion exchange resin column 7. In the case where such a product column is disposed, the product column consists of, for example, a distillation column such as a plate column or a packed column. In the case of adopting a plate column as the product column, the theoretical number of plates thereof is, for example, 5 to 50, and the reflux ratio is, for example, 0.5 to 3000 according to the theoretical number of plates. In the inside of the product column in the purification step, the column top pressure is set to, for example, −195 to 150 kPa (gauge pressure), and the column bottom pressure is higher than the column top pressure and is set to, for example, −190 to 180 kPa (gauge pressure). In the inside of the product column, the column top temperature is, for example, a temperature of higher than the boiling point of water and lower than the boiling point of acetic acid at the set column top pressure and is set to 50 to 150° C., and the column bottom temperature is, for example, a temperature of higher than the boiling point of acetic acid at the set column bottom pressure and is set to 70 to 160° C. A simple distiller (evaporator) may be used in place of the product column or the finishing column.

In the case of disposing the product column, the whole or a portion of the fourth acetic acid stream (liquid) from the ion exchange resin column 7 is continuously introduced to the product column. A vapor as an overhead stream containing a very small amount of lower boiling point components (e.g., methyl iodide, water, methyl acetate, dimethyl ether, crotonaldehyde, acetaldehyde, and formic acid) is continuously withdrawn from the column top of such a product column. This vapor is separated into a condensate portion and a gaseous portion in a predetermined condenser. A portion of the condensate portion is continuously refluxed to the product column, and another portion of the condensate portion may be recycled to the reaction vessel 1 or discarded to the outside of the system, or both. The gaseous portion is fed to the scrubber system 8. A bottom fraction containing a very small amount of higher boiling point components is continuously withdrawn from the column bottom of the product column. This bottom fraction is recycled to, for example, the second acetic acid stream in the line 34 before introduction to the distillation column 6. A side stream (liquid) is continuously withdrawn as a fifth acetic acid stream from the height position between the column top and the column bottom of the product column. The withdrawal position of the side stream from the product column is lower than, for example, the introduction position of the fourth acetic acid stream to the product column in the height direction of the product column. The fifth acetic acid stream is more enriched with acetic acid than the fourth acetic acid stream continuously introduced to the product column. Specifically, the acetic acid concentration of the fifth acetic acid stream is higher than the acetic acid concentration of the fourth acetic acid stream. The acetic acid concentration of the fifth acetic acid stream is, for example, 99.9 to 99.999% by mass or not less than this range as long as being higher than the acetic acid concentration of the fourth acetic acid stream. The hexyl iodide concentration in the fifth acetic acid stream is normally not more than 1 ppb by mass, but may be, for example, 0 to 30 ppb by mass, and particularly 0.01 to 10 ppb by mass (e.g., 0.1 to 5 ppb by mass). This fifth acetic acid stream is retained in, for example, a product tank (not shown). The ion exchange resin column 7 may be placed downstream of the product column instead of (or in addition to) its placement downstream of the distillation column 6 to treat the acetic acid stream from the product column.

EXAMPLES

Hereinafter, the present invention will be described in more detail with reference to Examples. However, the present invention is not intended to be limited by these Examples. The units %, ppm, and ppb are each expressed in terms of mass. A water concentration was measured by the Karl Fischer water determination method, metal ion concentrations were measured by ICP analysis (or atomic adsorption analysis), and concentrations of other components were measured by gas chromatography.

Comparative Example 1

In a continuous reaction process for producing acetic acid, methanol and carbon monoxide were continuously reacted in a carbonylation reactor, the reaction mixture from the reactor was continuously fed into a flasher, a volatile component containing at least acetic acid, methyl acetate, methyl iodide, water, and hydrogen iodide produced by flash distillation was fed to a first distillation column (lower boiling point component removal column), a first lower boiling point component was separated as an overhead, and a stream containing a large amount of components with a higher boiling point than acetic acid was separated as a bottom fraction from the column bottom. The overhead fraction (first lower boiling point component) was directly recycled to the reactor, and the bottom fraction from the column bottom was mixed with the bottom fraction of the flasher and recycled to the reactor. Then a first liquid stream portion was withdrawn from a side stream of the first distillation column, passed through a pipe made of a stainless steel material (SUS316: not more than 2% of Mn, 10 to 14% of Ni, 16 to 18% of Cr, 2 to 3% of Mo, and not less than 50% of Fe), and continuously fed into a second distillation column (dehydration column) (actual number of plates: 50, plate spacing between a feeding plate and a column top vapor withdrawal plate: 15 plates in terms of actual plates) made of the SUS316 material. The composition of the first liquid stream portion was 2% of methyl iodide, 2% of methyl acetate, 1% of water, 9,100 ppb of iron ions, 4,000 ppb of chromium ions, 2,500 ppb of nickel ions, 1,700 ppb of molybdenum ions, 410 ppb of zinc ions, 51 ppb of hexyl iodide, and acetic acid as a balance (including a very small amount of impurities). In the dehydration column, distillation was carried out under conditions of a column top temperature of 165° C. and a column bottom temperature of 175° C., a water-containing second lower boiling point component was concentrated at the column top, and a second liquid stream portion (purified acetic acid) was obtained as a bottom fraction. The distillate from the column top was recycled to the reactor. Based on an amount fed into the dehydration column of 1, the amount of the bottom fraction was 0.7 and the amount of the distillate from the column top was 0.3. The composition of the bottom fraction was 500 ppm of water, 21,000 ppb of iron ions, 8,300 ppb of chromium ions, 5,200 ppb of nickel ions, 2,800 ppb of molybdenum ions, 590 ppb of zinc ions, 50 ppb of hexyl iodide, and acetic acid as a balance (including a very small amount of impurities). The bottom fraction was cooled to 40 to 50° C., and then passed through a two meter long silver-substituted ion exchange resin (IER) column to adsorb and remove the hexyl iodide in the acetic acid. The flow rate of the bottom fraction [amount of bottom fraction treated (m$^3$/h) per cubic meter of resin] was 3.8 m$^3$/h·m$^3$ (resin volume). After the silver-substituted ion exchange resin treatment, the silver ion concentration of the product acetic acid was 41 ppb, the iron ion concentration was 100 ppb, the chromium ion concentration was 15 ppb, the nickel ion concentration was 10 ppb, the molybdenum ion concentration was 6 ppb, the zinc ion concentration was 7 ppb, and the hexyl iodide concentration was less than 5 ppb (not more than the limit of detection). The IER resin life (operating time until the hexyl iodide concentration at the resin outlet exceeds 5 ppb) under this operation was 1.2 years.

Comparative Example 2

The same experiment as in Comparative Example 1 was conducted except that: the material of the dehydration column was changed to a nickel base alloy [Hastelloy B2 (HB2): 28% of Mo, 69% of Ni, not more than 1% of Cr, not more than 2% of Fe, not more than 1% of Co, and not more than 1% of Mn]; the operating conditions of the dehydration column were set to a column top temperature of 160° C. and a column bottom temperature of 170° C.; and the composition of the charging mixture fed to the dehydration column was 2% of methyl iodide, 2% of methyl acetate, 1% of water, 13,700 ppb of iron ions, 6,000 ppb of chromium ions, 3,800 ppb of nickel ions, 2,600 ppb of molybdenum ions, 620 ppb of zinc ions, 51 ppb of hexyl iodide, and acetic acid as a balance (including a very small amount of impurities). The composition of the bottom fraction of the dehydration column was 490 ppm of water, 19,700 ppb of iron ions, 8,700 ppb of chromium ions, 7,000 ppb of nickel ions, 4,300 ppb of molybdenum ions, 890 ppb of zinc ions, 51 ppb of hexyl iodide, and acetic acid as a balance (including a very small amount of impurities). Further, after the silver-substituted ion exchange resin treatment, the silver ion concentration of the product acetic acid was 30 ppb, the iron ion concentration was 80 ppb, the chromium ion concentration was 16 ppb, the nickel ion concentration was 15 ppb, the molybdenum ion concentration was 9 ppb, the zinc ion concentration was 9 ppb, and the hexyl iodide concentration was less than 5 ppb (not more than the limit of detection). The IER resin life under this operation was 1.1 years.

Comparative Example 3

The same experiment as in Comparative Example 1 was conducted except that the operating conditions of the dehydration column were set to a column top temperature of 160° C. and a column bottom temperature of 170° C.

The composition of the bottom fraction of the dehydration column was 490 ppm of water, 19,800 ppb of iron ions, 7,900 ppb of chromium ions, 4,900 ppb of nickel ions, 2,700 ppb of molybdenum ions, 590 ppb of zinc ions, 49 ppb of hexyl iodide, and acetic acid as a balance (including a very small amount of impurities). Further, after the silver-substituted ion exchange resin treatment, the silver ion concentration of the product acetic acid was 34 ppb, the iron ion concentration was 85 ppb, the chromium ion concentration was 14 ppb, the nickel ion concentration was 9 ppb, the molybdenum ion concentration was 7 ppb, the zinc ion concentration was 5 ppb, and the hexyl iodide concentration was less than 5 ppb (not more than the limit of detection). The IER resin life under this operation was 1.2 years.

Example 1

The same experiment as in Comparative Example 1 was conducted except that: the material of the dehydration column was changed to a nickel base alloy [Hastelloy B2 (HB2): 28% of Mo, 69% of Ni, not more than 1% of Cr, not more than 2% of Fe, not more than 1% of Co, and not more than 1% of Mn]; and the operating conditions of the dehydration column were set to a column top temperature of 160° C. and a column bottom temperature of 170° C.

The composition of the bottom fraction of the dehydration column was 490 ppm of water, 13,200 ppb of iron ions, 5,800 ppb of chromium ions, 5,200 ppb of nickel ions, 3,100 ppb of molybdenum ions, 590 ppb of zinc ions, 52 ppb of hexyl iodide, and acetic acid as a balance (including a very small amount of impurities). Further, after the silver-substituted ion exchange resin treatment, the silver ion concentration of the product acetic acid was 18 ppb, the iron ion concentration was 25 ppb, the chromium ion concentration was 9 ppb, the nickel ion concentration was 8 ppb, the molybdenum ion concentration was 6 ppb, the zinc ion concentration was 7 ppb, and the hexyl iodide concentration was less than 5 ppb (not more than the limit of detection). The IER resin life under this operation was 1.8 years.

Example 2

The same experiment as in Example 1 was conducted except that a mixture liquid of 2% of methyl iodide, 2% of methyl acetate, 1% of water, 500 ppb of iron ions, 280 ppb of chromium ions, 190 ppb of nickel ions, 110 ppb of molybdenum ions, 410 ppb of zinc ions, 51 ppb of hexyl iodide, and acetic acid as a balance (including a very small amount of impurities) obtained by passing the first liquid stream portion withdrawn from a side stream of the first distillation column (lower boiling point component removal column) through a pipe made of a nickel base alloy [Hastelloy B2 (HB2)] material was used as the charging mixture fed to the dehydration column.

The composition of the bottom fraction of the dehydration column was 490 ppm of water, 770 ppb of iron ions, 420 ppb of chromium ions, 1,900 ppb of nickel ions, 800 ppb of molybdenum ions, 590 ppb of zinc ions, 50 ppb of hexyl iodide, and acetic acid as a balance (including a very small amount of impurities). Further, after the silver-substituted ion exchange resin treatment, the silver ion concentration of the product acetic acid was 5 ppb, the iron ion concentration was 6 ppb, the chromium ion concentration was 6 ppb, the nickel ion concentration was 7 ppb, the molybdenum ion concentration was 4 ppb, the zinc ion concentration was 4 ppb, and the hexyl iodide concentration was less than 5 ppb (not more than the limit of detection). The IER resin life under this operation was 6.1 years.

Example 3

The same experiment as in Example 1 was conducted except that the material of the dehydration column was changed to a nickel base alloy [Hastelloy C (HC276): 16% of Mo, around 57% of Ni, 16% of Cr, 5% of Fe, not more than 2.5% of Co, and not more than 1% of Mn].

The composition of the bottom fraction of the dehydration column was 520 ppm of water, 13,300 ppb of iron ions, 6,400 ppb of chromium ions, 5,800 ppb of nickel ions, 3,100 ppb of molybdenum ions, 590 ppb of zinc ions, 48 ppb of hexyl iodide, and acetic acid as a balance (including a very small amount of impurities). Further, after the silver-substituted ion exchange resin treatment, the silver ion concentration of the product acetic acid was 16 ppb, the iron ion concentration was 28 ppb, the chromium ion concentration was 12 ppb, the nickel ion concentration was 13 ppb, the molybdenum ion concentration was 7 ppb, the zinc ion concentration was 4 ppb, and the hexyl iodide concentration was less than 5 ppb (not more than the limit of detection). The IER resin life under this operation was 1.7 years.

Example 4

The same experiment as in Comparative Example 1 was conducted except that the operating conditions of the dehydration column were set to a column top temperature of 155° C. and a column bottom temperature of 165° C.

The composition of the bottom fraction of the dehydration column was 490 ppm of water, 13,100 ppb of iron ions, 5,800 ppb of chromium ions, 3,600 ppb of nickel ions, 2,500 ppb of molybdenum ions, 590 ppb of zinc ions, 50 ppb of hexyl iodide, and acetic acid as a balance (including a very small amount of impurities). Further, after the silver-substituted ion exchange resin treatment, the silver ion concentration of the product acetic acid was 13 ppb, the iron ion concentration was 23 ppb, the chromium ion concentration was 8 ppb, the nickel ion concentration was 7 ppb, the molybdenum ion concentration was 5 ppb, the zinc ion concentration was 5 ppb, and the hexyl iodide concentration was less than 5 ppb (not more than the limit of detection). The IER resin life under this operation was 2.0 years.

[Discussion on Results]

From Example 1, it is evident that by setting the concentrations of specific metal ions in the charging mixture to the dehydration column to be not more than certain values, and by employing a nickel base alloy having high corrosion resistance for the material of the dehydration column, the amount of metal ions flowing into the dehydration column is reduced, and moreover, the elution of corroded metals from the dehydration column is suppressed, which enables the metal ion concentrations in the purified acetic acid obtained from the dehydration column to be greatly reduced. As a result, the amount of metal ions flowing to the subsequent adsorptive removal step of the organic iodine compound could be decreased, the amount of other metal ions exchanged for the silver ions in the silver-substituted ion exchange resin (IER) was reduced, and the IER life was very long, at 1.8 years. Further, the metal ion concentrations in the product acetic acid after the IER treatment decreased, and in conjunction with that the elution of silver ions also decreased. As a result, the quality of the product acetic acid improved. In contrast, in Comparative Example 2, the material of the dehydration column was the same nickel base alloy as in Example 1, but because there was a large amount of metal ions flowing into the dehydration column, there was a large amount of metal ions flowing to the adsorptive removal step, and hence the IER life was short, at 1.1 years. In addition, in Comparative Example 3, the metal ion concentrations in the charging mixture to the dehydration column were the same as those in Example 1, but because the dehydration column material was stainless steel, corroded metals were eluted from the dehydration column, thereby increasing the amount of metal ions flowing to the adsorptive removal step. As a result, the IER life was 1.2 years, which is a low result.

From Examples 1 and 2, even when the materials of the dehydration columns were the same, reducing the concentrations of the corroded metals by controlling the concentrations of those metals in the dehydration column charging mixture also reduced the concentrations of the corroded metals in the purified acetic acid obtained from the dehydration column, and substantially improved the resin life of the silver-substituted ion exchange resin used in the adsorptive removal step. Further, because the corroded metal ion concentrations and the silver ion concentration in the product acetic acid after the IER treatment also decreased, the quality of the acetic acid improved even more. The fact that the metal ion concentrations at the ion exchange resin column outlet were not so much different despite a wide gap between the metal concentrations in the ion exchange resin column charging mixture can be thought as being the result of the ion exchange resin having a sufficiently high exchange capacity and almost all of the metal ions flowing to the ion exchange resin column being removed. In addition, it may be considered that if the experiment is carried out for an even longer duration, in Example 1, which had high metal ion concentrations in the ion exchange resin column charging mixture, the metal ion concentrations at the ion exchange resin column outlet would increase at an earlier stage than in Example 2, which had lower metal ion concentrations.

From Examples 1 and 3, using "HB2", which has an even higher corrosion resistance among nickel base alloys, as the material for the dehydration column enabled elution of the corroded metals to be more suppressed. As a result, the corroded metal ion concentrations in the purified acetic acid obtained from the dehydration column decreased, and the IER resin life and the quality of the product acetic acid improved.

From Examples 1 and 4, reducing the operating temperature of the dehydration column reduced the amount of the corroded metals eluted, and improved the resin life of the ion exchange resin.

Because the distillation column material does not contain zinc, for all conditions, the increase in zinc ions is only the increase in concentration corresponding to the concentrating rate from the concentrating in the dehydration column, and the absolute amount of the zinc ions in the purified acetic acid was the same as that of the zinc ions fed into the dehydration column.

Summarizing Comparative Examples 1 to 3 and Examples 1 to 4, it is evident that the resin life of an ion exchange resin improves generally in proportion to the decrease in the metal ion concentrations in the ion exchange resin column charging mixture. However, the resin life is not completely proportional to the metal ion concentrations in the ion exchange resin column charging mixture. This is because the amount of organic iodine compounds, such as hexyl iodide, in the ion exchange resin column charging mixture and the amount of silver that is eluted into the acetic acid from the ion exchange resin also affect the resin life. However, it is evident that the metal ion concentrations in the ion exchange resin column charging mixture are one of the main factors in reduction of resin life.

The configuration of the present invention and variations thereof may be summarized as follows.

[1] A method for producing acetic acid, comprising:

a carbonylation reaction step of reacting methanol with carbon monoxide in a reaction vessel in the presence of a catalyst system containing a metal catalyst and methyl iodide as well as acetic acid, methyl acetate, and water to produce acetic acid;

an evaporation step of separating a reaction mixture obtained in the carbonylation reaction step into a vapor stream and a residual liquid stream in an evaporator;

a lower boiling point component removal step of separating the vapor stream by distillation into an overhead stream rich in at least one lower boiling point component selected from methyl iodide and acetaldehyde and a first acetic acid stream rich in acetic acid;

a dehydration step of separating the first acetic acid stream by distillation into an overhead stream rich in water and a second acetic acid stream more enriched with acetic acid than the first acetic acid stream; and an adsorptive removal step of treating the second acetic acid stream, or an acetic acid stream that has been more enriched with acetic acid by further purification of the second acetic acid stream, with an ion exchange resin, wherein a nickel base alloy or zirconium is used as a material of a distillation column in the dehydration step, and as metal ion concentrations in a charging mixture of the distillation column in the dehydration step, an iron ion concentration is less than 10,000 ppb by mass, a chromium ion concentration is less than 5,000 ppb by mass, a nickel ion concentration is less than 3,000 ppb by mass, and a molybdenum ion concentration is less than 2,000 ppb by mass.

[2] The method for producing acetic acid according to [1], wherein the catalyst system further contains an ionic iodide.

[3] The method for producing acetic acid according to [1] or [2], wherein a zinc ion concentration in the charging mixture of the distillation column in the dehydration step is less than 1,000 ppb by mass (preferably less than 800 ppb by mass, more preferably less than 650 ppb by mass, further preferably less than 500 ppb by mass, particularly preferably less than 410 ppb by mass, and especially less than 200 ppb by mass).

[4] The method for producing acetic acid according to any one of [1] to [3], wherein operating conditions of the distillation column in the dehydration step are a column top temperature of less than 165° C. and a column bottom temperature of less than 175° C.

[5] The method for producing acetic acid according to any one of [1] to [4], wherein an iron ion concentration in the second acetic acid stream obtained in the dehydration step is less than 21,000 ppb by mass (preferably less than 16,000 ppb by mass, more preferably less than 6,000 ppb by mass, further preferably less than 2,000 ppb by mass, and particularly preferably less than 200 ppb by mass).

[6] The method for producing acetic acid according to any one of [1] to [5], wherein as metal ion concentrations in the second acetic acid stream obtained in the dehydration step, an iron ion concentration is less than 21,000 ppb by mass (preferably less than 16,000 ppb by mass, more preferably less than 6,000 ppb by mass, further preferably less than 2,000 ppb by mass, and particularly preferably less than 200 ppb by mass), a chromium ion concentration is less than 7,100 ppb by mass (preferably less than 5,000 ppb by mass, more preferably less than 3,000 ppb by mass, further preferably less than 1,000 ppb by mass, and particularly preferably less than 100 ppb by mass), a nickel ion concentration is less than 4,000 ppb by mass (preferably less than 3,000 ppb by mass, more preferably less than 1,800 ppb by mass, further preferably less than 700 ppb by mass, and particularly preferably less than 70 ppb by mass), a molybdenum ion concentration is less than 3,000 ppb by mass (preferably less than 2,500 ppb by mass, more preferably less than 1,500 ppb by mass, further preferably less than 500 ppb by mass, and particularly preferably less than 50 ppb by mass), and a zinc ion concentration is less than 1,000 ppb by mass (preferably less than 850 ppb by mass, more preferably less than 710 ppb by mass, further preferably less than 410 ppb by mass, and particularly preferably less than 150 ppb by mass).

[7] The method for producing acetic acid according to any one of [1] to [6], wherein a plate spacing between a charging mixture feeding plate and a column top vapor withdrawal plate of the distillation column in the dehydration step is not less than one plate in terms of actual plates (preferably not less than 3 plates, more preferably not less than 5 plates, further preferably not less than 8 plates, and particularly preferably not less than 10 plates).

[8] The method for producing acetic acid according to any one of [1] to [7], wherein the material of a charging pipe to the distillation column in the dehydration step is a nickel base alloy or zirconium.

[9] The method for producing acetic acid according to any one of [1] to [8], wherein an iron ion concentration in the charging mixture of the distillation column in the dehydration step is less than 9,000 ppb by mass (preferably less than 5,000 ppb by mass, more preferably less than 3,000 ppb by mass, further preferably less than 1,500 ppb by mass, particularly preferably less than 800 ppb by mass, and especially less than 400 ppb by mass).

[10] The method for producing acetic acid according to any one of [1] to [9], wherein a chromium ion concentration in the charging mixture of the distillation column in the dehydration step is less than 4,000 ppb by mass (preferably less than 2,500 ppb by mass, more preferably less than 1,500 ppb by mass, further preferably less than 750 ppb by mass, particularly preferably less than 400 ppb by mass, and especially less than 200 ppb by mass).

[11] The method for producing acetic acid according to any one of [1] to [10], wherein a nickel ion concentration in the charging mixture of the distillation column in the dehydration step is less than 2,500 ppb by mass (preferably less than 2,000 ppb by mass, more preferably less than 1,000 ppb by mass, further preferably less than 500 ppb by mass, particularly preferably less than 250 ppb by mass, and especially less than 150 ppb by mass).

[12] The method for producing acetic acid according to any one of [1] to [11], wherein a molybdenum ion concentration in the charging mixture of the distillation column in the dehydration step is less than 1,700 ppb by mass (preferably less than 1,200 ppb by mass, more preferably less than 700 ppb by mass, further preferably less than 350 ppb by mass, and particularly preferably less than 170 ppb by mass).

[13] The method for producing acetic acid according to any one of [1] to [12], wherein a hexyl iodide concentration in the charging mixture of the distillation column in the dehydration step is 0.2 to 10,000 ppb by mass (preferably 1 to 1,000 ppb by mass, more preferably 2 to 100 ppb by mass, further preferably 3 to 50 ppb by mass, and particularly preferably 5 to 40 ppb by mass).
[14] The method for producing acetic acid according to any one of [1] to [13], wherein a hexyl iodide concentration in the second acetic acid stream obtained in the dehydration step is 0.2 to 10,000 ppb by mass (preferably 1 to 1,000 ppb by mass, more preferably 2 to 100 ppb by mass, further preferably 3 to 50 ppb by mass, and particularly preferably 5 to 40 ppb by mass).
[15] The method for producing acetic acid according to any one of [1] to [14], wherein the metal ion concentrations in the charging mixture of the distillation column in the dehydration step are controlled by not less than one method selected from the group consisting of:
(1) employing a metal having high corrosion resistance as the material of the charging pipe to the dehydration column;
(ii) providing an ion exchange resin (in particular, a cation exchange resin) column for adsorptive removal of the metal ions at a position between an outlet of a reaction vessel and an inlet of the dehydration column; and
(iii) using methanol having a very low metal ion content (e.g., zinc ion content) as methanol to be fed to the reaction vessel.
[16] The method for producing acetic acid according to any one of [1] to [15], wherein a concentration of hydrogen iodide in the reaction mixture is 0.01 to 2% by mass with respect to the whole liquid phase of the reaction mixture.
[17] The method for producing acetic acid according to any one of [1] to [16], wherein a hexyl iodide concentration in the reaction mixture is 0.1 to 10,000 ppb by mass (preferably 0.5 to 1,000 ppb by mass, more preferably 1 to 100 ppb by mass, and further preferably 2 to 50 ppb by mass) with respect to the whole liquid phase of the reaction mixture.
[18] The method for producing acetic acid according to any one of [1] to [17], wherein a hexyl iodide concentration in the vapor stream is 0.1 to 10,000 ppb by mass (preferably 0.5 to 1,000 ppb by mass, more preferably 1 to 100 ppb by mass, and further preferably 2 to 50 ppb by mass).
[19] A method for producing acetic acid, comprising, in a distillation column having a nickel base alloy or zirconium as a material and having a plate spacing between a charging mixture feeding plate and a column top vapor withdrawal plate of not less than one plate in terms of actual plates, feeding crude acetic acid having an iron ion concentration of less than 10,000 ppb by mass, a chromium ion concentration of less than 5,000 ppb by mass, a nickel ion concentration of less than 3,000 ppb by mass, a molybdenum ion concentration of less than 2,000 ppb by mass, a zinc ion concentration of less than 1,000 ppb by mass, a hexyl iodide concentration of less than 510 ppb by mass, and an acetic acid concentration of not less than 80% by mass into the charging mixture feeding plate via a charging pipe having a nickel base alloy or zirconium as a material, and conducting distillation at a column top temperature of less than 165° C. and a column bottom temperature of less than 175° C. to obtain an overhead stream rich in water and purified acetic acid having an iron ion concentration of less than 21,000 ppb by mass, a chromium ion concentration of less than 7,100 ppb by mass, a nickel ion concentration of less than 4,000 ppb by mass, a molybdenum ion concentration of less than 3,000 ppb by mass, and a zinc ion concentration of less than 1,000 ppb by mass.
[20] The method for producing acetic acid according to [19], wherein the iron ion concentration in the crude acetic acid is less than 9,000 ppb by mass (preferably less than 5,000 ppb by mass, more preferably less than 3,000 ppb by mass, further preferably less than 1,500 ppb by mass, particularly preferably less than 800 ppb by mass, and especially less than 400 ppb by mass).
[21] The method for producing acetic acid according to [19] or [20], wherein the chromium ion concentration in the crude acetic acid is less than 4,000 ppb by mass (preferably less than 2,500 ppb by mass, more preferably less than 1,500 ppb by mass, further preferably less than 750 ppb by mass, particularly preferably less than 400 ppb by mass, and especially less than 200 ppb by mass).
[22] The method for producing acetic acid according to any one of [19] to [21], wherein the nickel ion concentration in the crude acetic acid is less than 2,500 ppb by mass (preferably less than 2,000 ppb by mass, more preferably less than 1,000 ppb by mass, further preferably less than 500 ppb by mass, particularly preferably less than 250 ppb by mass, and especially less than 150 ppb by mass).
[23] The method for producing acetic acid according to any one of [19] to [22], wherein the molybdenum ion concentration in the crude acetic acid is less than 1,700 ppb by mass (preferably less than 1,200 ppb by mass, more preferably less than 700 ppb by mass, further preferably less than 350 ppb by mass, and particularly preferably less than 170 ppb by mass).
[24] The method for producing acetic acid according to any one of [19] to [23], wherein the hexyl iodide concentration in the crude acetic acid is 0.2 to 10,000 ppb by mass (preferably 1 to 1,000 ppb by mass, more preferably 2 to 100 ppb by mass, further preferably 3 to 50 ppb by mass, and particularly preferably 5 to 40 ppb by mass).
[25] The method for producing acetic acid according to any one of [19] to [24], wherein the zinc ion concentration in the crude acetic acid is less than 1,000 ppb by mass (preferably less than 800 ppb by mass, more preferably less than 650 ppb by mass, further preferably less than 500 ppb by mass, particularly preferably less than 410 ppb by mass, and especially less than 200 ppb by mass).
[26] The method for producing acetic acid according to any one of [19] to [25], wherein the iron ion concentration in the purified acetic acid is less than 16,000 ppb by mass (preferably less than 6,000 ppb by mass, more preferably less than 2,000 ppb by mass, and further preferably less than 200 ppb by mass).
[27] The method for producing acetic acid according to any one of [19] to [26], wherein the chromium ion concentration in the purified acetic acid is less than 5,000 ppb by mass (preferably less than 3,000 ppb by mass, more preferably less than 1,000 ppb by mass, and further preferably less than 100 ppb by mass).
[28] The method for producing acetic acid according to any one of [19] to [27], wherein the nickel ion concentration in the purified acetic acid is less than 3,000 ppb by mass (preferably less than 1,800 ppb by mass, more preferably less than 700 ppb by mass, and further preferably less than 70 ppb by mass).
[29] The method for producing acetic acid according to any one of [19] to [28], wherein the molybdenum ion concentration in the purified acetic acid is less than 2,500 ppb by mass (preferably less than 1,500 ppb by mass, more preferably less than 500 ppb by mass, and further preferably less than 50 ppb by mass).
[30] The method for producing acetic acid according to any one of [19] to [29], wherein the zinc ion concentration in the purified acetic acid is less than 850 ppb by mass (preferably less than 710 ppb by mass, more preferably less than 410 ppb by mass, and further preferably less than 150 ppb by mass).

INDUSTRIAL APPLICABILITY

The method for producing acetic acid according to the present invention can be utilized as an industrial method for producing acetic acid by a carbonylation process of a methanol method (methanol method acetic acid process).

REFERENCE SIGNS LIST

1: reaction vessel
2: evaporator
3, 5, and 6: distillation column
4: decanter
7: ion exchange resin column
8: scrubber system
9: acetaldehyde separation and removal system
16: reaction mixture feed line
17: vapor stream discharge line
18 and 19: residual liquid stream recycle line
54: carbon monoxide-containing gas introduction line
55 and 56: potassium hydroxide introduction line
57: catalyst circulating pump
91: distillation column (first acetaldehyde removal column)
92: extraction column
93: distillation column (second acetaldehyde removal column)
94: distillation column (extractive distillation column)
95: decanter
96: decanter
97: distillation column (acetaldehyde removal column)
98: distillation column (extractive distillation column)
99: decanter
200: chimney tray

The invention claimed is:

1. A method for producing acetic acid, comprising:
a carbonylation reaction step comprising reacting methanol with carbon monoxide in a reaction vessel in the presence of a catalyst system containing a metal catalyst and methyl iodide as well as acetic acid, methyl acetate, and water to produce acetic acid;
an evaporation step comprising separating a reaction mixture obtained in the carbonylation reaction step into a vapor stream and a residual liquid stream in an evaporator;
a lower boiling point component removal step comprising separating the vapor stream by distillation into an overhead stream rich in at least one lower boiling point component selected from methyl iodide and acetaldehyde and a first acetic acid stream rich in acetic acid;
a dehydration step comprising separating the first acetic acid stream by distillation into an overhead stream rich in water and a second acetic acid stream more enriched with acetic acid than the first acetic acid stream; and
an adsorptive removal step comprising treating the second acetic acid stream, or an acetic acid stream that has been more enriched with acetic acid by further purification of the second acetic acid stream, with an ion exchange resin,
wherein a nickel base alloy or zirconium is used as a material of a distillation column in the dehydration step, in the distillation column, a plate spacing between a charging mixture feeding plate and a column top vapor withdrawal plate is not less than one plate in terms of actual plates, and as metal ion concentrations in a charging mixture of the distillation column in the dehydration step, an iron ion concentration is less than 9,000 ppb by mass, a chromium ion concentration is less than 4,000 ppb by mass, a nickel ion concentration is less than 2,500 ppb by mass, a molybdenum ion concentration is less than 1,700 ppb by mass, and a zinc ion concentration is less than 800 ppb by mass, and
wherein the method includes, for controlling the metal ion concentrations in the charging mixture to be within the ranges, (i) employing a nickel base alloy or zirconium as the material of the charging pipe to the distillation column in the dehydration step; optionally (ii) providing an ion exchange resin column at a position between an outlet of the reaction vessel and an inlet of the distillation column in the dehydration step or an ion exchange resin vessel at a position between an outlet of the reaction vessel and an inlet of the distillation column in the dehydration step; and (iii) using methanol having a zinc ion content of less than 10 ppm by mass as the methanol to be fed to the reaction vessel.

2. The method for producing acetic acid according to claim 1, wherein the catalyst system further contains an ionic iodide.

3. The method for producing acetic acid according to claim 1, wherein a zinc ion concentration in the charging mixture of the distillation column in the dehydration step is less than 500 ppb by mass.

4. The method for producing acetic acid according to claim 1, wherein operating conditions of the distillation column in the dehydration step are a column top temperature of less than 165° C. and a column bottom temperature of less than 175° C.

5. The method for producing acetic acid according to claim 1, wherein an iron ion concentration in the second acetic acid stream obtained in the dehydration step is less than 21,000 ppb by mass.

6. The method for producing acetic acid according to claim 1, wherein as metal ion concentrations in the second acetic acid stream obtained in the dehydration step, an iron ion concentration is less than 21,000 ppb by mass, a chromium ion concentration is less than 7,100 ppb by mass, a nickel ion concentration is less than 4,000 ppb by mass, a molybdenum ion concentration is less than 3,000 ppb by mass, and a zinc ion concentration is less than 1,000 ppb by mass.

7. The method for producing acetic acid according to claim 1, wherein the material of a charging pipe to the distillation column in the dehydration step is a nickel base alloy or zirconium.

8. A method for producing acetic acid, comprising, in a distillation column having a nickel base alloy or zirconium as a material and having a plate spacing between a charging mixture feeding plate and a column top vapor withdrawal plate of not less than one plate in terms of actual plates, feeding crude acetic acid having an iron ion concentration of less than 9,000 ppb by mass, a chromium ion concentration of less than 4,000 ppb by mass, a nickel ion concentration of less than 2,500 ppb by mass, a molybdenum ion concentration of less than 1,700 ppb by mass, a zinc ion concentration of less than 800 ppb by mass, a hexyl iodide concentration of less than 510 ppb by mass, and an acetic acid concentration of not less than 80% by mass into the charging mixture feeding plate via a charging pipe having a nickel base alloy or zirconium as a material, and conducting distillation at a column top temperature of less than 165° C.

and a column bottom temperature of less than 175° C. to obtain an overhead stream rich in water and purified acetic acid having an iron ion concentration of less than 21,000 ppb by mass, a chromium ion concentration of less than 7,100 ppb by mass, a nickel ion concentration of less than 4,000 ppb by mass, a molybdenum ion concentration of less than 3,000 ppb by mass, and a zinc ion concentration of less than 1,000 ppb by mass, and wherein the method includes, for controlling the metal ion concentrations in the charging mixture to be within the ranges, (i) employing a nickel base alloy or zirconium as the material of the charging pipe to the distillation column; optionally (ii) providing an ion exchange resin column at a position between an outlet of a reaction vessel and an inlet of the distillation column or an ion exchange resin vessel at a position between an outlet of a reaction vessel and an inlet of the distillation column; and (iii) using methanol having a zinc ion content of less than 10 ppm by mass as the methanol to be fed to a reaction vessel.

9. The method for producing acetic acid according to claim 1, wherein the iron ion concentration in the charging mixture of the distillation column in the dehydration step is less than 400 ppb by mass.

10. The method for producing acetic acid according to claim 8, wherein the crude acetic acid has an iron ion concentration of less than 3,000 ppb by mass.

11. The method for producing acetic acid according to claim 1, wherein operating condition of the distillation column in the dehydration step is a column bottom temperature of less than 173° C.

12. The method for producing acetic acid according to claim 8, wherein operating condition of the distillation column is a column bottom temperature of less than 173° C.

13. The method for producing acetic acid according to claim 1, wherein the chromium ion concentration in the charging mixture of the distillation column in the dehydration step is less than 200 ppb by mass.

14. The method for producing acetic acid according to claim 8, wherein the crude acetic acid has a chromium ion concentration of less than 1,500 ppb by mass.

15. The method for producing acetic acid according to claim 1, wherein the nickel ion concentration in the charging mixture of the distillation column in the dehydration step is less than 150 ppb by mass.

16. The method for producing acetic acid according to claim 8, wherein the crude acetic acid has a nickel ion concentration of less than 1,000 ppb by mass.

17. The method for producing acetic acid according to claim 1, wherein the molybdenum ion concentration in the charging mixture of the distillation column in the dehydration step is less than 170 ppb by mass.

18. The method for producing acetic acid according to claim 8, wherein the crude acetic acid has a molybdenum ion concentration of less than 700 ppb by mass.

19. The method for producing acetic acid according to claim 8, wherein the crude acetic acid has a zinc ion concentration of less than 650 ppb by mass.

20. The method for producing acetic acid according to claim 1, wherein as metal ion concentrations in the second acetic acid stream obtained in the dehydration step, an iron ion concentration is less than 200 ppb by mass, a chromium ion concentration is less than 100 ppb by mass, a nickel ion concentration is less than 70 ppb by mass, a molybdenum ion concentration is less than 50 ppb by mass, and a zinc ion concentration is less than 150 ppb by mass.

* * * * *